(12) United States Patent
Eickelmann et al.

(10) Patent No.: US 12,115,179 B2
(45) Date of Patent: *Oct. 15, 2024

(54) PHARMACEUTICAL COMPOSITION, METHODS FOR TREATING AND USES THEREOF

(71) Applicant: Boehringer Ingelheim International GmbH, Ingelheim am Rhein (DE)

(72) Inventors: Peter Eickelmann, Mittelbiberach (DE); Michael Mark, Biberach an der Riss (DE); Leo John Seman, Cheshire, CT (US); Leo Thomas, Biberach an der Riss (DE); Uli Christian Broedl, Oakville (CA); Rolf Grempler, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,462

(22) Filed: May 19, 2023

(65) Prior Publication Data

US 2023/0285432 A1  Sep. 14, 2023

Related U.S. Application Data

(63) Continuation of application No. 17/176,450, filed on Feb. 16, 2021, now abandoned, which is a continuation of application No. 16/452,719, filed on Jun. 26, 2019, now abandoned, which is a continuation of application No. 13/912,599, filed on Jun. 7, 2013, now Pat. No. 10,406,172, which is a continuation of application No. 12/703,988, filed on Feb. 11, 2010, now abandoned.

(60) Provisional application No. 61/152,302, filed on Feb. 13, 2009.

(51) Int. Cl.
| | |
|---|---|
| *A61K 31/7048* | (2006.01) |
| *A61K 31/00* | (2006.01) |
| *A61K 31/155* | (2006.01) |
| *A61K 31/198* | (2006.01) |
| *A61K 31/341* | (2006.01) |
| *A61K 31/351* | (2006.01) |
| *A61K 31/39* | (2006.01) |
| *A61K 31/403* | (2006.01) |
| *A61K 31/4439* | (2006.01) |
| *A61K 31/522* | (2006.01) |
| *A61K 31/70* | (2006.01) |
| *A61K 31/7004* | (2006.01) |
| *A61K 31/7008* | (2006.01) |
| *A61K 45/06* | (2006.01) |

(52) U.S. Cl.
CPC .......... *A61K 31/7048* (2013.01); *A61K 31/00* (2013.01); *A61K 31/155* (2013.01); *A61K 31/198* (2013.01); *A61K 31/341* (2013.01); *A61K 31/351* (2013.01); *A61K 31/39* (2013.01); *A61K 31/403* (2013.01); *A61K 31/4439* (2013.01); *A61K 31/522* (2013.01); *A61K 31/70* (2013.01); *A61K 31/7004* (2013.01); *A61K 31/7008* (2013.01); *A61K 45/06* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 4,802,924 A | 2/1989 | Woznicki et al. |
| 5,807,580 A | 9/1998 | Luber |
| 6,303,661 B1 | 10/2001 | Demuth et al. |
| 6,340,475 B2 | 1/2002 | Shell et al. |
| 6,348,090 B1 | 2/2002 | Grillo et al. |
| 6,414,126 B1 | 7/2002 | Ellsworth et al. |
| 6,448,323 B1 | 9/2002 | Jordan et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

US Department of Health and Human Services, FDA, Center for Drug Evaluation and Research "Application No. 204629Orig1s000 Summary Review (Jardiance) " 2014, 20 pages.

U.S. Appl. No. 15/380,272, filed Dec. 15, 2016. Non-Final Office Action mailed Mar. 5, 2019. 18 pgs.

Valentine, Virginia "The Role of the Kidney and Sodium-Glucose Cotransporter-2 Inhibition in Diabetes Management" (2012) Clinical Diabetes, vol. 30, No. 4, 151-155.

(Continued)

*Primary Examiner* — Traviss C McIntosh, III
(74) *Attorney, Agent, or Firm* — David L. Kersher

(57) ABSTRACT

The invention relates to a pharmaceutical composition comprising an SGLT2 inhibitor, a DPPIV inhibitor and a third antidiabetic agent which is suitable in the treatment or prevention of one or more conditions selected from type 1 diabetes mellitus, type 2 diabetes mellitus, impaired glucose tolerance and hyperglycemia. In addition the present invention relates to methods for preventing or treating of metabolic disorders and related conditions.

24 Claims, 1 Drawing Sheet

(56) References Cited

U.S. PATENT DOCUMENTS

| | | |
|---|---|---|
| 6,794,480 B2 | 9/2004 | Goto et al. |
| 6,890,898 B2 | 5/2005 | Bachovchin et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,109,192 B2 | 9/2006 | Hauel et al. |
| 7,169,761 B2 | 1/2007 | Tomiyama et al. |
| 7,173,028 B2 | 2/2007 | Dahmann et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,482,337 B2 | 1/2009 | Himmelsbach et al. |
| 7,501,426 B2 | 3/2009 | Himmelsbach et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,820,815 B2 | 10/2010 | Pfrengle et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 9,155,705 B2 | 10/2015 | Friedl et al. |
| 9,555,001 B2 | 1/2017 | Ito et al. |
| 9,949,997 B2 | 4/2018 | Broedl et al. |
| 9,949,998 B2 | 4/2018 | Broedl et al. |
| 10,258,637 B2 | 4/2019 | Broedl et al. |
| 10,406,172 B2 * | 9/2019 | Eickelmann ............ A61P 13/04 |
| 10,596,120 B2 | 3/2020 | Ito et al. |
| 10,610,489 B2 | 4/2020 | Schneider et al. |
| 2001/0041674 A1 | 11/2001 | Tomiyama et al. |
| 2001/0044435 A1 | 11/2001 | Himmelsbach et al. |
| 2001/0053791 A1 | 12/2001 | Babcock et al. |
| 2002/0137903 A1 | 9/2002 | Ellsworth et al. |
| 2002/0173509 A1 | 11/2002 | Himmelsbach et al. |
| 2002/0198205 A1 | 12/2002 | Himmelsbach et al. |
| 2003/0064935 A1 | 4/2003 | Gougoutas |
| 2003/0087843 A1 | 5/2003 | Washburn |
| 2003/0104053 A1 | 6/2003 | Gusler et al. |
| 2003/0105077 A1 | 6/2003 | Kanstrup et al. |
| 2003/0114390 A1 | 6/2003 | Washburn et al. |
| 2004/0037883 A1 | 2/2004 | Zhou et al. |
| 2004/0087587 A1 | 5/2004 | Himmelsbach et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0180925 A1 | 9/2004 | Matsuno et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0130985 A1 | 6/2005 | Himmelsbach et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2005/0234108 A1 | 10/2005 | Himmelsbach et al. |
| 2005/0256310 A1 | 11/2005 | Hulin et al. |
| 2006/0002998 A1 | 1/2006 | Trehan et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0079541 A1 | 4/2006 | Langkopf et al. |
| 2006/0142210 A1 | 6/2006 | Eckhardt et al. |
| 2006/0142310 A1 | 6/2006 | Pfrengle et al. |
| 2006/0154866 A1 | 7/2006 | Chu et al. |
| 2006/0189548 A1 | 8/2006 | Himmelsbach et al. |
| 2006/0205711 A1 | 9/2006 | Himmelsbach et al. |
| 2006/0210627 A1 | 9/2006 | Pfeffer et al. |
| 2006/0234953 A1 | 10/2006 | Himmelsbach et al. |
| 2006/0247226 A1 | 11/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0027168 A1 | 2/2007 | Pfrengle et al. |
| 2007/0049537 A1 | 3/2007 | Eckhardt et al. |
| 2007/0054867 A1 | 3/2007 | Eckhardt et al. |
| 2007/0060530 A1 | 3/2007 | Christopher et al. |
| 2007/0072813 A1 | 3/2007 | Himmelsbach et al. |
| 2007/0073046 A1 | 3/2007 | Eckhardt et al. |
| 2007/0077296 A1 | 4/2007 | Folger et al. |
| 2007/0212411 A1 | 9/2007 | Fawzy |
| 2007/0249544 A1 | 10/2007 | Himmelsbach et al. |
| 2007/0259821 A1 | 11/2007 | Eckhardt et al. |
| 2007/0259900 A1 | 11/2007 | Sieger et al. |
| 2007/0264370 A1 | 11/2007 | Jeffers |
| 2007/0281940 A1 | 12/2007 | Dugi et al. |
| 2007/0293690 A1 | 12/2007 | Tomiyama et al. |
| 2007/0299076 A1 | 12/2007 | Piotrowski et al. |
| 2008/0058379 A1 | 3/2008 | Eckhardt et al. |
| 2008/0107731 A1 | 5/2008 | Kohlrausch et al. |
| 2008/0108816 A1 | 5/2008 | Zutter |
| 2008/0193529 A1 | 8/2008 | Kowalski et al. |
| 2008/0207882 A1 | 8/2008 | Derdau et al. |
| 2008/0221174 A1 | 9/2008 | Grenier et al. |
| 2008/0234367 A1 | 9/2008 | Washburn et al. |
| 2008/0249089 A1 | 10/2008 | Himmelsbach et al. |
| 2008/0255159 A1 | 10/2008 | Himmelsbach et al. |
| 2008/0287529 A1 | 11/2008 | Deshpande et al. |
| 2009/0023913 A1 | 1/2009 | Eckhardt et al. |
| 2009/0137801 A1 | 5/2009 | Himmelsbach et al. |
| 2009/0192314 A1 | 7/2009 | Pfrengle et al. |
| 2009/0226517 A1 | 9/2009 | Vyas et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0092124 A1 | 4/2010 | Magnusson et al. |
| 2010/0093654 A1 | 4/2010 | Himmelsbach et al. |
| 2010/0099641 A1 | 4/2010 | Himmelsbach et al. |
| 2010/0173916 A1 | 7/2010 | Himmelsbach et al. |
| 2010/0179191 A1 | 7/2010 | Himmelsbach et al. |
| 2010/0204250 A1 | 8/2010 | Himmelsbach et al. |
| 2010/0209506 A1 | 8/2010 | Eisenreich |
| 2010/0210662 A1 | 8/2010 | Baroni et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2010/0330177 A1 | 12/2010 | Pourkavoos |
| 2011/0014284 A1 | 1/2011 | Eisenreich et al. |

(56) References Cited

U.S. PATENT DOCUMENTS

| | | |
|---|---|---|
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0178033 A1 | 7/2011 | Eckhardt et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237532 A1 | 9/2011 | De Vries et al. |
| 2011/0237789 A1 | 9/2011 | Weber et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0196812 A1 | 8/2012 | Eickelmann et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0283169 A1 | 11/2012 | Grempler et al. |
| 2012/0296080 A1 | 11/2012 | Eckhardt et al. |
| 2012/0296091 A1 | 11/2012 | Sieger et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2016/0000816 A1 | 1/2016 | Broedl et al. |
| 2016/0235680 A1 | 8/2016 | Ito et al. |
| 2017/0020907 A1 | 1/2017 | Eickelmann et al. |
| 2017/0095424 A1 | 4/2017 | Ito et al. |
| 2017/0305952 A1 | 10/2017 | Klein et al. |
| 2018/0104249 A1 | 4/2018 | Eisenreich |
| 2018/0169126 A1 | 6/2018 | Broedl et al. |
| 2018/0177794 A1 | 6/2018 | Wienrich et al. |
| 2018/0185291 A1 | 7/2018 | Ito et al. |
| 2018/0193427 A1 | 7/2018 | Grempler et al. |
| 2018/0200278 A1 | 7/2018 | Broedl et al. |
| 2018/0289678 A1 | 10/2018 | Eisenreich et al. |
| 2018/0344647 A1 | 12/2018 | Boeck et al. |
| 2019/0038654 A1 | 2/2019 | Broedl et al. |
| 2019/0298749 A1 | 10/2019 | Mayoux et al. |
| 2019/0309004 A1 | 10/2019 | Wirth et al. |
| 2020/0069713 A1 | 3/2020 | Eickelmann et al. |
| 2020/0085851 A1 | 3/2020 | Eickelmann et al. |
| 2020/0138770 A1 | 5/2020 | von Eynatten et al. |
| 2020/0138844 A1 | 5/2020 | Broedl et al. |
| 2020/0188306 A1 | 6/2020 | Schneider et al. |
| 2020/0222423 A1 | 7/2020 | Wienrich et al. |
| 2020/0268777 A1 | 8/2020 | Broedl et al. |
| 2020/0297639 A1 | 9/2020 | Ito et al. |
| 2020/0360412 A1 | 11/2020 | Broedl et al. |
| 2020/0368261 A1 | 11/2020 | Broedl et al. |
| 2020/0397809 A1 | 12/2020 | Mayoux |
| 2020/0397867 A1 | 12/2020 | Grempler et al. |
| 2021/0059974 A1 | 3/2021 | Broedl et al. |
| 2021/0267902 A1 | 9/2021 | Ito et al. |
| 2022/0105043 A1 | 4/2022 | Boeck et al. |
| 2024/0115506 A1 | 4/2024 | Boeck et al. |

FOREIGN PATENT DOCUMENTS

| | | |
|---|---|---|
| CA | 2437240 A1 | 8/2002 |
| CA | 2435730 A1 | 9/2002 |
| CA | 2463989 A1 | 4/2003 |
| CA | 2494177 A1 | 2/2004 |
| CA | 2496249 A1 | 3/2004 |
| CA | 2505389 A1 | 5/2004 |
| CA | 2470365 A1 | 6/2004 |
| CA | 2508024 A1 | 6/2004 |
| CA | 2508226 A1 | 6/2004 |
| CA | 2508233 A1 | 6/2004 |
| CA | 2526145 A1 | 9/2004 |
| CA | 2539032 A1 | 3/2005 |
| CA | 2544480 A1 | 6/2005 |
| CA | 2548353 A1 | 7/2005 |
| CA | 2555050 A1 | 9/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2576294 A1 | 3/2006 |
| CA | 2574500 A1 | 4/2006 |
| CA | 2586938 A1 | 5/2006 |
| CA | 2617090 A1 | 2/2007 |
| CA | 2649922 A1 | 11/2007 |
| CA | 2651019 A1 | 11/2007 |
| CA | 2651089 A1 | 11/2007 |
| CA | 2696579 A1 | 2/2009 |
| CA | 2720450 A1 | 10/2009 |
| CA | 2726244 A1 | 12/2009 |
| CA | 2732803 A1 | 2/2010 |
| CA | 2735562 A1 | 2/2010 |
| CA | 2736421 A1 | 3/2010 |
| CA | 2738367 A1 | 4/2010 |
| CA | 2745037 A1 | 7/2010 |
| CA | 2745039 A1 | 7/2010 |
| CA | 2750798 A1 | 8/2010 |
| CA | 2752437 A1 | 8/2010 |
| CA | 2776296 A1 | 4/2011 |
| CA | 2782179 A1 | 6/2011 |
| CN | 101234105 A | 8/2008 |
| DE | 2758025 A1 | 7/1979 |
| DE | 2951135 A1 | 6/1981 |
| DE | 102004044221 A1 | 3/2006 |
| EP | 0206567 A2 | 12/1986 |
| EP | 1224195 B | 7/2002 |
| EP | 1344780 A1 | 9/2003 |
| EP | 1354888 A1 | 10/2003 |
| EP | 1385856 A | 2/2004 |
| EP | 1406873 A2 | 4/2004 |
| EP | 1500403 A1 | 1/2005 |
| EP | 1523994 A1 | 4/2005 |
| EP | 1553094 A1 | 7/2005 |
| EP | 1564210 A1 | 8/2005 |
| EP | 1586571 A1 | 10/2005 |
| EP | 1791852 A2 | 6/2007 |
| EP | 1852108 A1 | 11/2007 |
| EP | 1852439 A1 | 11/2007 |
| EP | 2143443 A1 | 1/2010 |
| EP | 2166007 A1 | 3/2010 |
| EP | 1609785 B1 | 2/2016 |

(56) References Cited

FOREIGN PATENT DOCUMENTS

| | | | |
|---|---|---|---|
| JP | 55007256 A | 1/1980 |
| JP | 56039056 A | 4/1981 |
| JP | 58164502 | 9/1983 |
| JP | 62030750 A | 2/1987 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| KR | 20070111099 A | 11/2007 |
| WO | 9605873 A1 | 2/1996 |
| WO | 9718814 A1 | 5/1997 |
| WO | 9831697 A1 | 7/1998 |
| WO | 2001016147 A1 | 3/2001 |
| WO | 2001027128 A1 | 4/2001 |
| WO | 2001052825 A2 | 7/2001 |
| WO | 2001074834 A1 | 10/2001 |
| WO | 200197808 A1 | 12/2001 |
| WO | 200202560 A2 | 1/2002 |
| WO | 2002053573 A1 | 7/2002 |
| WO | 2002064606 A1 | 8/2002 |
| WO | 2002068420 A1 | 9/2002 |
| WO | 2002083066 A2 | 10/2002 |
| WO | 2003004496 A1 | 1/2003 |
| WO | 2003020737 A1 | 3/2003 |
| WO | 2003024965 A2 | 3/2003 |
| WO | 2003031458 A1 | 4/2003 |
| WO | 2003032997 A1 | 4/2003 |
| WO | 2003035177 A2 | 5/2003 |
| WO | 2003037327 A1 | 5/2003 |
| WO | 2003057200 A2 | 7/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004041820 A1 | 5/2004 |
| WO | 2004046115 A1 | 6/2004 |
| WO | 2004050658 A1 | 6/2004 |
| WO | 2004052902 A1 | 6/2004 |
| WO | 2004052903 A1 | 6/2004 |
| WO | 2004063209 A2 | 7/2004 |
| WO | 2004065380 A1 | 8/2004 |
| WO | 2004076470 A2 | 9/2004 |
| WO | 2004080990 A1 | 9/2004 |
| WO | 2005000848 A1 | 1/2005 |
| WO | 2005011786 A1 | 2/2005 |
| WO | 2005012318 A2 | 2/2005 |
| WO | 2005012326 A1 | 2/2005 |
| WO | 2005021566 A2 | 3/2005 |
| WO | 2005049022 A2 | 6/2005 |
| WO | 2005051950 A1 | 6/2005 |
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |
| WO | 2005092877 A1 | 10/2005 |
| WO | 2005116014 A1 | 12/2005 |
| WO | 2005117861 A1 | 12/2005 |
| WO | 2006002912 A1 | 1/2006 |
| WO | 2006005613 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006024024 A2 | 3/2006 |
| WO | 2006029769 A1 | 3/2006 |
| WO | 2006034489 A2 | 3/2006 |
| WO | 2006037537 A2 | 4/2006 |
| WO | 2006040625 A1 | 4/2006 |
| WO | 2006047248 A1 | 5/2006 |
| WO | 2006048427 A1 | 5/2006 |
| WO | 2006064033 A2 | 6/2006 |
| WO | 2006072334 A2 | 7/2006 |
| WO | 2006076231 A2 | 7/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2006135693 A2 | 12/2006 |
| WO | 2007000445 A1 | 1/2007 |
| WO | 2007014886 A1 | 2/2007 |
| WO | 2007014894 A2 | 2/2007 |
| WO | 2007014895 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007035665 A1 | 3/2007 |
| WO | 2007039417 A1 | 4/2007 |
| WO | 2007041053 A2 | 4/2007 |
| WO | 2007071738 A1 | 6/2007 |
| WO | 2007078726 A2 | 7/2007 |
| WO | 2007093610 A1 | 8/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128749 A1 | 11/2007 |
| WO | 2007128761 A2 | 11/2007 |
| WO | 2007136151 A1 | 11/2007 |
| WO | 2007144175 A2 | 12/2007 |
| WO | 2007149797 A2 | 12/2007 |
| WO | 2008017670 A1 | 2/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008093878 A1 | 8/2008 |
| WO | 2008093882 A1 | 8/2008 |
| WO | 2008101938 A1 | 8/2008 |
| WO | 2008101939 A1 | 8/2008 |
| WO | 2008101943 A1 | 8/2008 |
| WO | 2008113000 A1 | 9/2008 |
| WO | 2008116179 A1 | 9/2008 |
| WO | 2008131149 A2 | 10/2008 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009035969 A1 | 3/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010092163 A2 | 8/2010 |
| WO | 2010138535 A1 | 12/2010 |

(56) References Cited

FOREIGN PATENT DOCUMENTS

| | | | |
|---|---|---|---|
| WO | 2010140111 A1 | 12/2010 | |
| WO | 2010147768 A1 | 12/2010 | |
| WO | 2011039107 A1 | 4/2011 | |
| WO | 2011039108 A2 | 4/2011 | |
| WO | 2011039337 A1 | 4/2011 | |
| WO | 2011039367 A2 | 4/2011 | |
| WO | 2011060256 A2 | 5/2011 | |
| WO | 2011060290 A2 | 5/2011 | |
| WO | 2011064352 A1 | 6/2011 | |
| WO | 2011113947 A1 | 9/2011 | |
| WO | 2011117295 A1 | 9/2011 | |
| WO | 2011120923 A1 | 10/2011 | |
| WO | 2011138380 A1 | 11/2011 | |
| WO | 2011138421 A1 | 11/2011 | |
| WO | 2011161161 A1 | 12/2011 | |
| WO | 2011163206 A2 | 12/2011 | |
| WO | 2012031124 A2 | 3/2012 | |
| WO | 2012062698 A1 | 5/2012 | |
| WO | 2012065993 A1 | 5/2012 | |
| WO | 2012106303 A1 | 8/2012 | |
| WO | 2012107476 A1 | 8/2012 | |
| WO | 2012120040 A1 | 9/2012 | |
| WO | 2013131967 A1 | 9/2013 | |
| WO | 2013139777 A1 | 9/2013 | |
| WO | 2014011926 A1 | 1/2014 | |
| WO | 2016059219 A1 | 4/2016 | |

OTHER PUBLICATIONS

Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Wang et al., "Modern diagnosis and treatment of common cardiovascular diseases", Jul. 31, 2013, Shanxi Science and Technology Press, 1st Edition, p. 32 (English Abstract).

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Weber, Ann E. "Dipeptidyl Peptidase IV Inhibitors for the Treatment of Diabetes" (2004) J. Med. Chem., 47, 4135-4141.

Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.

Wielert-Badt, Susanne et al. "Probing the Conformation of the Sugar Transport Inhibitor Phlorizin by 2D-NMR, Molecular Dynamics Studies, and Pharmacophore Analysis" (2000) J. Med. Chem., vol. 43, 1692-1698.

Wielert-Badt, Susanne et al. "Single Molecule Recognition of Protein Binding Epitopes in Brush Border Membranes by Force Microscopy" (2002) Biophysical Journal, vol. 82, 2767-2774.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Woo, Vincent C. "Dapagliflozin: where does it fit in the treatment of type 2 diabetes" (2009) Expert Opinion on Pharmacotherapy, 10(15): 2527-2535.

www.who.int/medicinedocs/index/assoc/s14141e/s14141e.pdf Addendum 1 to "The use of stems in the selection of International Nonproprietary names (INN) for pharmaceutical substances" World Health Organization Jun. 19, 2007, pp. 1-3, XP007906327.

Xue, Song., et al; Zinc-mediated Synthesis of Alpha-C-Glycosided from 1,2-Anhydroglycosides; Synletters (2003) vol. 6 pp. 870-872.

Yamada, Yuichiro et al. "Clinic: Careful Progress in the Field and new Therapeutic Methods" Medical Online, (2007) vol. 220, No. 13, pp. 1219-1221.

Zhang, L. et al."Dapagliflozin treatment in patients with different stages of type 2 diabetes mellitus: effects on glycaemic control and body weight" Diabetes, Obesity and Metabolism (2010) vol. 12, No. 6, p. 510-515.

Zhang, Qiang et al. "Pharmaceuticals" Peking University Medical Press, Jan. 2005, first edition, partial English language translation, pp. 171-177.

Zimmermann, Grant R et al. "Multi-target therapeutics: when the whole is greater than the sum of the parts" (2007) Drug Discovery Today, vol. 12, 34-42.

Derosa, Giuseppe et al. "Optimizing combination treatment in the management of type 2 diabetes" (2007) Vascular Health and Risk Management, 3(5), pp. 665-671.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Downes, Martin J. et al. "Triple therapy in type 2 diabetes; a systematic review and network meta-analysis" (2015) Peer J, 3:e1461, 21 pgs.

Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.

Drug Watch "Type 2 Diabetes Mellitus" Formulary vol. 43 Aug. 2008 p. 304.

DrugBank entries for Linagliptin (Accession No. DB08882), Sitagliptin (Accession No. DB01261) and Vitagliptin (Accession No. DB04876), downloaded Jan. 30, 2018, 12 pgs.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Eckhardt, M. et al., "8-(3-(R)-Aminopiperidin-1-yl)-7-but-2-ynyl-3-methyl-1-(4-methyl-quinazolin-2-ylmethyl)-3,7-dihydropurine-2,6-dione (BI1356), a Highly Potent, Selective, Long-Acting, and Orally Bioavailable DPP-4 Inhibitor for the Treatment of Type 2 Diabetes" J. Med Chem (2007) vol. 50, pp. 6450-6453.

European Medicines Agency, Science Medicines Health, "Assessment Report Forxiga dapagliflozin" (2012) 170 pgs.

FDA Formal Comments on "Draft Guidance for Industry on Powder Blends and Finished Dosage Units—Stratified In-Process Dosage Unit Sampling and Assessment" Jan. 21, 2004, 54 pgs.

Ferrannini, Ele et al. "Metabolic response to sodium-glucose cotransporter 2 inhibition in type 2 diabetic patients" (2014) The Journal of Clinical Investigation vol. 124, No. 2, 499-508 and article amendment, p. 1868.

Ferrannini, Ele et al. "SGLT2 inhibition in diabetes mellitus: rationale and clinical prospects" (2012) Nat. Rev. Endocrinol. vol. 8, 495-502.

Fiese, Eugene F et al. "Preformulation" (1987) The Theory and Practice of Industrial Pharmacy, 28 pgs.

Final Office Action mailed Dec. 10, 2012, U.S. Appl. No. 12/703,988, filed Feb. 11, 2010. Inventor: Peter Eickelmann.

Final Office Action mailed Dec. 3, 2019, U.S. Appl. No. 15/380,272, filed Dec. 15, 2016. Inventor: Masanori Ito.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No 1, pp. 268-276.

Gallwitz, B. "Sitagliptin with Metformin: Profile of a Combination for the Treatment of Type 2 Diabetes". Drugs of Today, Oct. 2007, 43(10), p. 681-689.

Gallwitz, Baptist "Saxagliptin, a dipeptidyl peptidase IV inhibitor for the treatment of type 2 diabetes" IDrugs (2008) 11(12), pp. 906-917.

Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.

(56) References Cited

OTHER PUBLICATIONS

Gennaro, Alfonso R. "Remington: The Science and Practice of Pharmacy" Twentieth Edition (2000) 4 pgs.
Gerich, John E. "Matching Treatment to Pathophysiology in Type 2 Diabetes" (2001) Clinical Therapeutics, vol. 23, No. 5, 646-659.
Ghassemi et al. "Synthesis and properties of new sulfonated poly(p-phenylene) derivatives for proton exchange membranes" Polymer (2004) pp. 5847-5854.
Ghosh, Raktim Kumar et al. "SGLT2 Inhibitors: A New Emerging Therapeutic Class in the Treatment of Type 2 Diabetes Mellitus" (2012) Journal of Clinical Pharmacology, 52, 457-463.
Golay A. et al. "Link Between Obesity and Type 2 Diabetes" (2005) Best Practice & Research Clinical Endocrinology & Metabolism, vol. 19, No. 4, 649-663.
Goldstein, Barry J. "Insulin Resistance as the Core Defect in Type 2 Diabetes Mellitus" (2002) Am J. Cardiol, 90 (suppl): 3G-10G.
Goldstein, Barry J. et al. "Effect of Initial Combination Therapy with Sitagliptin, a Dipeptidyl Peptidase-4 Inhibitor and Metformin on Glycemic Control in Patients with Type 2 Diabetes" (2007) Diabetes Care, vol. 30, No. 8, 1979-1987.
Graefe-Mody et al., "The novel DPP-4 inhibitor . . . " Diabetes, (online) 2008, XP002561421 http://professional.diabetes.org/content/posters/2008/p553-p.pdf.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Green, Brian D. et al."Dipeptidyl peptidase IV (DPP IV) inhibitors: a newly emerging drug class for the treatment of type 2 diabetes" (2006) Diabetes and Vascular Disease Research, 159-165.
Guillory, J. Keith "Generation of Polymorphs, Hydrates, Solvates and Amorphous Solids" Polymorphism in Pharmaceutical Solids (1999) 46 pgs.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Gwaltney, S. "Medicinal Chemistry Approaches to the Inhibition of Dipeptidyl Peptidase IV", Current Topics in Medicinal Chemistry, 2008, 8, p. 1545-1552.
Halimi, S. "Metformin: 50 years old, fit as a fiddle, and indispensable for its pivotal role in type 2 diabetes management" (2006) 32, 555-556.
Halimi, Serge, et al. "Combination treatment in the management of type 2 diabetes: focus on vildagliptin and metformin as a single tablet" (2008) Vascular Health and Risk Management, 4(3) 481-492.
Handlon, Anthony L. "Sodium glucose co-transporter 2 (SGLT2) inhibitors as potential antidiabetic agents" (2005) Expert Opinion on Therapeutic Patents, 15:11, 1531-1540.
Hansch, C. "Search for New Drugs, Use of Quantitative Structure—Activity Relationships (QSAR) In Drug Design" (1980) Pomona College, Clermont, CA, Translated from Khimiko-Farmatsevticheskii Zhurnal, vol. 14, No. 10, 15-30.
Harris, Maureen I. "Classification, Diagnostic Criteria, and Screening for Diabetes" (1995) Diabetes in America, 2nd Edition, pp. 15-36.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
Heise, Tim et al. "Treatment with BI 1356, a Novel and Potent DPP-IV Inhibitor Significantly Reduces Glucose Excursions after an OGTT in Patients with Type 2 Diabetes" (2007) Diabetes, Supp 1, vol. 56, 4 pgs.
Henry Ford Health System, "Chronic Kidney Disease, Clinical Practice Recommendations for Primary Care Physicians and Healthcare Providers, A Collaborative Approach", (Edition 6.0), 76 pgs.
Hermansen, K. et al. "Efficacy and safety of the dipeptidyl peptidase-4 inhibitor, sitagliptin, in patients with type 2 diabetes mellitus inadequately controlled on glimepiride alone or on glimepiride and metformin" (2007) Diabetes, Obesity and Metabolism, 9, 733-745.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Hummel, Charles S. et al. "Glucose transport by human renal Na+/D-glucose co-transporters" (2010) Am J Physiol Cell Physiol, 34 pgs.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Huttner, S. et al. "Safety, Tolerability, Pharmacokinetics, and Pharmacodynamics of Single Oral Doses of BI 1356, and Inhibitor of Dipeptidyl Peptidase 4, in Healthy Male Volunteers" Journal of Clinical Pharmacology (2008) V 48, pp. 1171-1178.
Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Idris, Iskandar et al "Sodium-glucose co-transporter-2 inhibitors: an emerging new class of oral antidiabetic drug" (2009) Diabetes, Obesity and Metabolism, 11, 79-88.
Abdul-Ghani, Muhammad "Where does Combination Therapy with an SGLT2 Inhibitor Plus a DPP-4 Inhibitor Fit in the Management of Type 2 Diabetes?" (2015) Diabetes Care, 38, 373-375.
Abdul-Ghani, Muhammad A. et al. "Role of Sodium-Glucose Cotransporter 2 (SGLT 2) Inhibitors in the Treatment of Type 2 Diabetes" (2011) Endocrine Reviews, 32(4), 515-531.
Abstract in English for KR20070111099, Nov. 11, 2007.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Ahren B: "DPP-4 inhibitors", Best practice and research in clinical endocrinology and metabolism—New therapies for diabetes Dec. 2007 GB LNKD—DOI:10.1016/J. Beem.2007.07.005, vol. 21, No. 4, Dec. 2007, pp. 517-533.
Ahren, Bo "Dipeptidyl Peptidase-4 Inhibitors" (2007) Diabetes Care, vol. 30, No. 6, 1344-1350.
Ahren, Bo "Novel Combination Treatment of Type 2 Diabetes DPP-4 Inhibition + Metformin" (2008) Vascular Health and Risk Management, 4(2), 383-394.
Ahren, Bo et al. "Twelve- and 52-Week Efficacy of the Dipeptidyl Peptidase IV Inhibitor LAF237 in Metformin-Treated Patients with Type 2 Diabetes" (2004) Diabetes Care, vol. 27, No. 12, 2874-2880.
American Diabetes Association "Standards of Medical Care in Diabetes-2009" (2009) Diabetes Care, vol. 32, Supplement 1, S-13-S61.
Ashiya, Mona et al. "Non-insulin therapies for type 2 diabetes" (2007) Nature Reviews, Drug Discovery vol. 6, 777-778.
Augeri, David J. "Discovery and Preclinical Profile of Saxagliptin (BMS-477118): A Highly Potent, Long-Acting, Orally Active Dipeptidyl Peptidase IV Inhibitor for the Treatment of Type 2 Diabetes" J. Med. Chem. (2005) vol. 48, pp. 5025-5037.
Aulinger, B.A. et al., "Ex-4 and the DPP-IV Inhibitor Vildagliptin have Additive Effects to Suppress Food Intake in Rodents". Abstract No. 1545-P, 2008.
Ault Addison, "Techniques and experiments for organic chemistry" University Science Books, 1998, pp. 59-60.
Aulton, Michael E. "Pharmaceutics, The Science of Dosage Form Design" (2002) 2nd Edition, 404-409.

(56) References Cited

OTHER PUBLICATIONS

Baati, Rachid et al. "A Convenient Synthesis of 2-Tetrahydrofuranyl Ethers" (2000) Organic Letters, vol. 2, No. 4, 485-487.
Baggio, Laurie L. et al. "Biology of Incretins: GLP-1 and GIP" Gastroenterology (2007) vol. 132, 2131-2157.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Boehringer Ingelheim, "BI Trial No. 1275.1 Final Analysis" Clinical Study Synopsis for Public Disclosure, (2013) UNo. U13-2755-01, 38 pgs.
Brazg, R et al. "Effect of Adding MK-0431 to Ongoing Metformin Therapy in Type 2" (2005) Diabetes, vol. 54, Suppl. 1, A3.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Bristol-Myers Squibb Company, Label "Glucophage (metformin hydrochloride) Tablets, Glucophage XR (metformin hydrochloride) Extended-Release Tablets" Apr. 2017, 35 pgs.
British National Formulary (2008) "6. Endrocrine system" 2 pgs.
Byrn, Stephen et al. "Pharmaceutical Solids: A Strategic Approach to Regulatory Considerations" Pharmaceutical Research, vol. 12, No. 7, (1995) pp. 945-954.
Caira, Mino R. "Crystalline Polymorphism of Organic Compounds" (1998) Topics in Current Chemistry, vol. 198, 164-208.
Campbell, R. Keith "Rationale for Dipeptidyl Peptidase 4 Inhibitors: A New Class of Oral Agents for the Treatment of Type 2 Diabetes Mellitus" (2007) The Annals of Pharmacotherapy, vol. 41, 51-60.
CAS Registry No. 668270-12-0; STN database entered Mar. 28, 2004. 5 pgs.
Castaneda, Francisco et al. "Thioglycosides as inhibitors of hSGLT1 and hSGLT2: Potential therapeutic agents for the control of hyperglycemia in diabetes" International Journal of Medical Sciences (2007) 4(3), pp. 131-139.
Charpentier, Guillaume "Oral combination therapy for type 2 diabetes" (2002) Diabetes Metab Res Rev, vol. 18, S70-S76.
Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].
Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00328172 "Efficacy and Safety of 3 Doses of BI1356 (Linagliptin) in Type 2 Diabetes Patients" Sponsor: Boehringer Ingelheim, Last Update Posted Mar. 14, 2014, 4 pgs.
Clinical Trials: NCT00554450 "Renal Impairment in Type 2 Diabetic Subjects" Sponsor: AstraZeneca, Last Update Posted Oct. 17, 2016, 5 pgs.
Clinical Trials: NCT00602472. "BI 1356 in Combination with Metformin and a Sulphonylurea in Type 2 Diabetes". ClinicalTrials.gov processed: Jan. 14, 2009 3 pgs.
Clinical Trials: NCT00602472. "BI 1356 in combination with metformin and a sulphonylurea in Type 2 Diabetes". DrugLib.com, Nov. 3, 2008. http://www.druglib.com/trial/08/NCT00309608.html.
Clinical Trials: NCT00602472. "History of Changes for Study: NCT00602472. BI 1356 in Combination with Metformin and a Sulphonylurea in Type 2 Diabetes". Submitted Date: Feb. 11, 2009 7 pgs.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Clinical Trials: NCT01064414 "An Efficacy, Safety and Tolerability Stude of Canagliflozin in Patients with Type 2 Diabetes Mellitus who have Moderate Renal Impairment" Sponsor: Janssen Research & Development LLC, Last Update Posted Aug. 14, 2013, 7 pgs.
Clinical Trials: NCT01210001 "Efficacy and Safety of Empagliflozin (BI 10773) in Type 2 Diabetes Patients on a Background of Pioglitazone Alone or with Metformin" Sponsor: Boehringer Ingelheim, Last Update Posted Jun. 17, 2014, 7 pgs.
Clinical Trials: NCT01422876 "Efficacy and Safety of Empagliflozin (BI 10773) / Linagliptin (BI 1356) Fixed Dose Combination in Treatment naive and Metformin Treated Type 2 Diabetes Patients" Sponsor: Boehringer Ingelheim Pharmaceuticals, Apr. 1, 2015, 4 pgs.
Colorcon; Opadry II Aqueous Film Coating; http://www.colorcon.com/products-formulation/all-products/film-coatings/immediate-release/opadry-II ; Dec. 31, 2015.
Conarello, S.L. et al., "Mice lacking dipeptidyl peptidase IV are protected against obesity and insulin resistance". PNAS, May 27, 2003, vol. 100, No. 11, p. 6825-6830.
Consoli, A. et al. "Initiating oral glucose-lowering therapy with metformin in type 2 diabetic patients: an evidence-based strategy to reduce the burden of late-developing diabetes complications" (2004) Diabetes Metab, 30, 509-516.
Cornell, Susan "Vildagliptin (LAF 237): A Dipeptidyl Peptidase IV Inhibitor for the Treatment of Type 2 Diabetes Mellitus" (2006) J Pharm Technol, vol. 22, pp. 105-109.
Crepaldi, G. et al. "Dipeptidyl peptidase 4 (DPP-4) inhibitors and their role in Type 2 diabetes management" (2007) J. Endocrinol. Invest., 30, 610-614.
Deacon, Carolyn F. "Perspectives in Diabetes Therapeutic Strategies Based on Glucagon-Like Peptide 1" Diabetes, (2004) vol. 53 pp. 2181-2189.
Defronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.
Rosenstock, Julio et al. "Dual Add-on Therapy in Type 2 Diabetes Poorly Controlled with Metformin Monotherapy: A Randomized Double-Blind Trial of Saxagliptin Plus Dapagliflozin Addition Versus Single Additon of Saxagliptin or Dapagliflozin to Metformin" (2015) Diabetes Care, vol. 38: 376-383.
Rudnic, Edward et al. "Oral Solid Dosage Forms" Remington—The Science and Practice of Pharmacy, 21th Ed, (2005) Chapter 45, Multiple Compressed Tablets, p. 890.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Salgado Junior, et al. "Nonalcoholic fatty liver disease and obesity" Acti Cirugica Brasiliera (2006) vol. 21, Supp. 1, pp. 72-78.
Scheen, Andre J. "Pharmacokinetic considerations for the treatment of diabetes in patients with chronic kidney disease" (2013) Expert Opinion on Drug Metabolism and Toxicology, 9:5, 529-550.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 613-615.

(56) References Cited

OTHER PUBLICATIONS

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Scottish Medicines Consortium, Product Assessment "dapagliflozin 5mg and 10mg (Forxiga)" Sep. 2012, 14 pgs.
Setter, Stephen M. et al. "Metformin Hydrochloride in the Treatment of Type 2 Diabetes Mellitus: A Clincial Review with a Focus on Dual Therapy" (2003) Clincial Therapeutics, vol. 25, No. 12, 2991-3026.
Sherwin, Robert S. et al. "The Prevention or Delay of Type 2 Diabetes" Diabetes Care, (2002) vol. 25, No. 4, pp. 742-749.
Shin-Yakuzaigaku Souron. Edited by Sadasuke Okano, published by Nankodo. 1987, vol. 3, pp. 255-256.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Softeland, Eirik et al. "Empagliflozin as Add-on Therapy in Patients with Type 2 Diabetes Inadequately Controlled With Linagliptin and Metformin: A 24-Week Randomized, Double-Blind, Parallel-Group Trial" (2016) Diabetes Care, DOI:10.2337/dc16-1347, pp. 1-9.
Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.
Song, Fujian et al. "What is indirect comparsion?" (2009) Hayward Medical Communications, www.whatisseries.co.uk, 6 pgs.
Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.
Stern, Judith et al. "Insulin Resistance and Pancreatic Insulin Release in Genetically Obese Zucker Rat" (1972) P.S.E.B.M., vol. 139, 66-69.
Strack, Thomas "Metformin: A Review" (2008) Drugs of Today, 44(4), 303-314.
Takebayashi, Kohzo et al. "Effect of Sodium Glucose Cotransporter 2 Inhibitors With Low SGLT2/SGLT1 Selectivity on Circulating Glucagon-Like Peptide 1 Levels in Type 2 Diabetes Mellitus" (2017) J Clin Med Res., vol. 9, (9) 745-753.
Tanaka, Chikako "Therapeutic Drugs for Metabolic Diseases, Chapter 2" (2002) New Yakurigaku (New Pharmacology) pp. 524-527.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
The Merck Manual Diagnosis and Therapy; Seventeenth Edition; "13 / Disorders of Carbohyrate Metabolism" Merck Research Laboratories (1999) pp. 165-177.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo "Long-term treatment with empagliflozin, a novel, potent and selective SGLT-2 inhibitor, improves glycaemic control and features of metabolic syndrome in diabetic rats" (2012) Diabetes, Obesity and Metabolism, vol. 14, No. 1, 94-96.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Threlfall, Terry "Structural and Thermodynamic Explanations of Ostwald's Rule" Organic Process Research & Development (2003) vol. 7, pp. 1017-1027.
Tinahones, Francisco J. et al. "Linagliptin as add-on to empagliflozin and metformin in patients with type 2 diabetes: Two 24-week randonmized double-blind, double-dummy parallel-group trials" (2017) Diabetes Obes Metab, 19(2): 266-274.
Torrance, Christopher J. et al. "Combinatorial chemoprevention of intestinal neoplasia" (2000) Nature Medicine, vol. 6, No. 8, 1024-1028.
Turner, Robert C. et al. "Glycemic Control with Diet, Sulfonylurea, Metformin or Insulin in Patients with Type 2 Diabetes Mellitus, Progressive Requirement for Multiple Therapies (UKPDS-49)" (1999) American Medical Association, vol. 281, No. 21, 8 pgs.
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
U.S. Appl. No. 13/287,216, filed Nov. 2, 2011. Inventor: Rolf Grempler.
U.S. Appl. No. 13/367,739, filed Feb. 7, 2012. Inventor: Thomas Klein.
U.S. Appl. No. 13/413,702, filed Mar. 7, 2012. Inventor: Masanori Ito.
U.S. Appl. No. 13/484,506, filed May 31, 2012. Inventor: Marion Wienrich.
U.S. Appl. No. 13/539,713, filed Jul. 2, 2012. Inventor: Uli Broedl.
U.S. Appl. No. 13/634,886, filed Sep. 14, 2012. Inventor: Peter Eickelmann.
U.S. Appl. No. 13/637,413, filed Sep. 26, 2012. Inventor: Rolf Grempler.
U.S. Appl. No. 13/693,239, filed Dec. 4, 2012. Inventor: Klaus Dugi.
U.S. Appl. No. 13/695,492, filed Oct. 31, 2012. Inventor: Thomas Klein.
U.S. Appl. No. 13/785,365, filed Mar. 5, 2013. Inventor: Masanori Ito.
U.S. Appl. No. 13/833,097, filed Mar. 15, 2013. Inventor: Eric Williams Mayoux.
U.S. Appl. No. 14/244,196, filed Apr. 3, 2014. Inventor: Uli Christian Broedl.
U.S. Appl. No. 14/244,208, filed Apr. 3, 2014. Inventor: Uli Christian Broedl.
U.S. Appl. No. 14/253,935, filed Apr. 16, 2014. Inventor: Uli Christian Broedl.
Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
US Department of Health and Human Services, CDER, FDA, "Guideline for Submitting Supporting Documentation in Drug Applications for the Manufacture of Drug Substances" Feb. 1987, 48 pages.
US Department of Health and Human Services, FDA, Endocrinologic and Metabolic Drugs Advisory Committee; Notice of Meeting, Federal Register, vol. 76, No. 80, Apr. 26, 2011, 23324-23325.
US Department of Health and Human Services, FDA, "Guidance for Industry, Diabetes Mellitus—Evaluating Cardiovascular Risk in New Antidiabetic Therapies to Treat Type 2 Diabetes" Dec. 2008, 8 pages.
US Department of Health and Human Services, FDA, "Guidance for Industry, Pharmacokinetics in Patients with Impaired Renal Function—Study Design, Data Analysis, and Impact on Dosing and Labeling" May 1998, 19 pages.
Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
International Search Report and Written Opinion for PCT/EP2012/053910 mailed May 14, 2012.
International Search Report for PCT/EP2005/002618 mailed Jun. 30, 2005.
International Search Report for PCT/EP2005/056806 mailed Dec. 27, 2006.

(56) References Cited

OTHER PUBLICATIONS

International Search Report for PCT/EP2006/061520 mailed Jul. 26, 2006.
International Search Report for PCT/EP2006/061956 mailed on Jul. 5, 2006.
International Search report for PCT/EP2006/061957 mailed on Jul. 5, 2006.
International Search Report for PCT/EP2006/062191 mailed Aug. 8, 2006.
International Search Report for PCT/EP2006/064702 mailed on Jul. 26, 2007.
International Search Report for PCT/EP2006/065710 mailed Mar. 8, 2007.
International Search Report for PCT/EP2006/066107 mailed Jan. 11, 2007.
International Search Report for PCT/EP2006/066347 mailed Mar. 7, 2007.
International Search Report for PCT/EP2007/051411 mailed on May 2, 2007.
International Search Report for PCT/EP2007/054248 mailed on Jun. 18, 2007.
International Search Report for PCT/EP2007/062023 mailed Sep. 17, 2008.
International Search Report for PCT/EP2008/060736 mailed Nov. 28, 2008.
International Search Report for PCT/EP2008/060744 mailed Dec. 5, 2008.
International Search Report for PCT/EP2010/051735 mailed May 20, 2010.
International Search Report for PCT/EP2010/051736 mailed May 7, 2010.
International Search Report for PCT/EP2011/054734 mailed Aug. 12, 2011.
International Search Report for PCT/EP2011/069532 mailed Dec. 15, 2011.
International Search Report for PCT/EP2012/052108 mailed Mar. 8, 2012.
International Search Report for PCT/EP2012/053910 mailed May 14, 2012.
International Search Report for PCT/EP2013/054524 mailed on May 6, 2013.
International Search Report PCT/EP2016/079465 filed on Dec. 1, 2016.
Inzucchi, Silvo E. "Oral Antihyperglycemic Therapy for Type 2 Diabetes" (2002) JAMA, vol. 287, No. 3, 360-372.
Isaji, Masayuki "Sodium-glucose cotransporter inhibitors for diabetes" Current Opinion in Investigational Drugs, (2007) vol. 8, No. 4, pp. 285-292.
Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.
Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Johnson & Johnson "FDA Advisory Committee Recommends Approval of Canagliflozin for Treatment of Adults with Type 2 Diabetes" (2013) Press Release, 3 pgs.
Kadowaki, T et al. "PPAR gamma agonist and antagonist" Nihon Yakurigaku Zasshi (2001) vol. 118, No. 9, pp. 321-326. (English abstract).
Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.
Klepser, Teresa B. et al. "Metformin hydrochloride: An antihyperglycemic agent" (1997) Am J Health-Syst Pharm, vol. 54, 893-903.
Knochel, Paul et al. "Highly functionalized Organomagnesium Reagents Prepared through Halogen-Metal Exchange" Angew. Chem. INt. Ed. (2003) vol. 42, 4302-4320.
Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Krasovskiy Arkady et al. "A LiCL-Mediated Br/Mg Exchange Reaction for the Preparation of Functionalized Aryl- and Heterarylmagnesium Compounds from Organic Bromides**" Angew. Chem. Int. Ed. (2004) vol. 43, pp. 3333-3336.
Kuribayashi, Takeshi., et al; Bis C-Glycosylated Diphenylmethanes for Stable Glycoepitope Mimetics; Syntletters (1999) vol. 6 pp. 737-740.
Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Langley, Alissa K. et al. "Dipeptidyl Peptidase IV Inhibitors and the Incretin System in Type 2 Diabetes Mellitus" (2007) Pharmacotherapy, vol. 27, 1164-1180.
Larsen, Mogens Lytken et al. "Effect of Long-Term Monitoring of Glycosylated Hemoglobin Levels in Insulin-Dependent Diabetes Mellitus" (1990) The New England Journal of Medicine, vol. 323, No. 15, 1021-1025.
Lebovitz, Harold E. "Insulin secretagogues: old and new" (1999) Diabetes Review, vol. 7, 139-153.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Levetan, Claresa "Oral antidiabetic agents in type 2 diabetes" (2007) Current Medical Research and Opinion, vol. 23, No. 4, 945-952.
Levey, Andrew S. et al. "Definition and classification of chronic kidney disease: A position statement from Kidney Disease: Improving Global Outcomes (KDIGO)" (2005) Kidney International, vol. 67, 2089-2100.
Levien,T.L. et al., "New drugs in development for the treatment of diabetes", Diabetes Spectrum, American Diabetes Association, US, vol. 22, No. 2, Jan. 1, 2009, pp. 92-106.
Lewin, Andrew et al "Initial Combination of Empagliflozin and Linagliptin in Subjects with Type 2 Diabetes" (2015) Diabetes Care, vol. 38, 394-402.
Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.
Li, Yazhou, et al. "Glucagon-like Peptide-1 Receptor Signaling Modulates b Cell Apoptosis" (2003) The Journal of Biological Chemistry, vol. 278, No. 1, 471-478.
Nathan, D. M., et al., "Management of hyperglycemia in type 2 diabetes mellitus: a consensus algorithm for the initiation and adjustment of therapy" (2008) Diabetologia, vol. 51, No. 1, 8-11.
Lieberman, Herbert A. et al. "Pharmaceutical Dosage Forms: Tablets, vol. 1" (1989) pp. 5-6.
Lipworth, Brian J. "Clinical pharmacology of b3-adrenoceptors" Br J Clin Pharmacol (1996) pp. 291-300.
Lu, Jiangqian et al. "Chapter 8, Treatment of heart failure iwth clinical conditions, Section II Treatment of heart failure complicated by arrhythmia" Feb. 28, 2015, Practical Handbook of Diagnosis and Treatment of Heart Failure, People's Military Medical Publishing House 1st Edition, p. 177 (English Abstract).
Matsuyama, Tatsuo et al. "Glucagon-like peptide-1 (7-36 amide): a potent glucagonostatic and insulinotropic hormone" Diabetes Research and Clincial Practice (1988) 5, 281-284.
McHale, Mary "Grignard Reaction" Connexions module: m15245, (2007) pp. 1-18.

(56) References Cited

OTHER PUBLICATIONS

McKinney, James D. et al. "The Practice of Structure Activity Relationships (SAR) in Toxicology" (2000) Toxicological Sciences, vol. 56, 8-17.
McLaughlin, Mark., et al; Suzuki-Miyaura Cross-Coupling of Benzylic Phospahates with Arylboronic Acids; Organic Letters (2005) vol. 7 No. 22 pp. 4875-4878.
McMaster University, Chem2006 Lab Manual, 1997/98, Expt 1, Part B, pp. 1-9.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.
Meng, Wei et al."Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual of Diagnosis and Therapy, 17th Edition, (1999) Ch 13 / Disorders of Carohydrate Metabolism, Diabetes Mellitus. pp. 165-177.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.
Merriam-Webster's Collegiate Dictionary, published 1998 by Merriam-Webster Inc. "prevent".
Meyer, Timothy W. "Tubular injury in glomerular disease" (2003) Kidney International, vol. 63, p. 774-787.
Mojsov, Svetlana "Insulinotropin: Glucagon-like Peptide I (7-37) Co-encoded in the Glucagon Gene Is a Potent Stimulator of Insulin Release in the Perfused Rat Pancreas" J. Clin. Invest. (1987) vol. 79, 616-619.
Mooradian, Arsharg D. et al. "Narrative Review: A Rational Approach to Starting Insulin Therapy" (2006) Annals of Internal Medicine, vol. 145, pp. 125-134.
Munir, Kashif et al. "Differential pharmacology and clinical utility of empagliflozin in type 2 diabetes" (2016) Clinical Pharmacology: Advances and Applications, vol. 8, 19-34.
Nathan, D.M. et al. "Medical management of hyperglycemia in type 2 diabetes mellitus: a consensus algorithm for the initiation and adjustment of therapy" Diabetologia (2009) 52, 17-30.
Nathan, David M. et al. "Management of Hyperglycemia in Type 2 Diabetes: A Consensus Algorithm for the Initiation and Adjustment of Therapy" (2006) Diabetes Care, vol. 29, No. 8, 1963-1972.
Nathan, David M. et al. "Medical Management of Hyperglycemia in Type 2 Diabetes: A Consensus Algorithm for the Initiation and Adjustment of Therapy" (2009) vol. 32, No. 1, pp. 193-203.
Nathan, Medical Management of hyperglycemia in type 2 diabetes mellitus, Diabetologia, vol. 52, 2009, 14 pages.
National Institute for Health Research, Horizon Scanning Centre, "Empagliflozin for type 2 diabetes mellitus" Apr. 2012, 10 pgs.
National Kidney Foundation, "Clinical Practice Guidelines, For Chronic Kidney Disease: Evaluation, Classification and Stratification" (2002) 356 pgs.
Nauck, Michael A. et al. "Cardiovascular Actions and Clincial Outcomes with Glucagon-Like Peptide-1 Receptor Agonists and Dipeptidyl Peptidase-4 Inhibitors" Circulation (2017) vol. 136, 849-870.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Office Action mailed Feb. 16, 2012, US AppIn No. U.S. Appl. No. 12/703,988, filed Feb. 11, 2010. Inventor: Peter Eickelmann.
Office Action mailed Nov. 18, 2019, U.S. Appl. No. 15/778,294, filed May 23, 2018. Inventor: Georg Boeck.
Office Action mailed on Jun. 5, 2012. U.S. Appl. No. 12/673,319, filed Apr. 15, 2010. First named inventor: Klaus Dugi.
Office Action mailed Sep. 28, 2012. U.S. Appl. No. 12/704,019, filed Feb. 11, 2010. First named inventor: Wolfram Eisenreich.
Oku, Akira., et al; T-1095, An Inhibitor or renal Na+-Glucose Cotransporters, May Provide a Novel Approach to Treating Diabetes; Diabetes (1999) vol. 48 pp. 1794-1800.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Plosker, Greg L. "Dapagliflozin: A Review of Its Use in Patients with Type 2 Diabetes" (2014) Drugs, 74, 2191-2209.
Pratley, Richard E. et al. "Inhibition of DPP-4: a new therapeutic approach for the treatment of type 2 diabetes" (2007) Current Medical Research and Opinion, vol. 23, No. 4, 919-931.
Printz, Richard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Pschyrembel et al. Clinical Dictionary, 257th Edition, Diabetes Mellitus, (1993) 320-321.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Riddle, Matthew "Combining Sulfonylureas and Other Oral Agents" (2000) The American Journal of Medicine, vol. 108 (6A), 15S-22S.
Riddle, Matthew C. "Oral Pharmacologic Management of Type 2 Diabetes" (1999) American Family Physician, 60(9), 2613-2620.
Robinson, J.A. "Chemical and Biochemical Aspects of Polyether-Ionophore Antibiotic Biosynthesis" (1991) Progress in the Chemistry of Organic Natural Products, 1-81.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rosenstock, Julio et al. "Dipeptidyl peptidase-4 inhibitors and the management of type 2 diabetes mellitus" (2007) Current Opinion in Endocrinology, Diabetes & Obesity, vol. 14: 98--107.

* cited by examiner

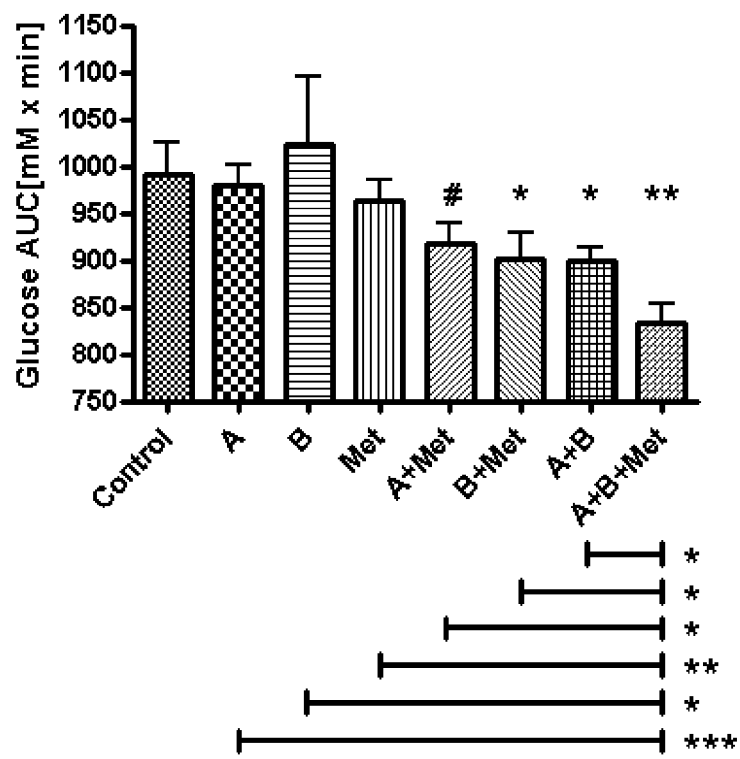

PHARMACEUTICAL COMPOSITION, METHODS FOR TREATING AND USES THEREOF

This application is a continuation application of U.S. application Ser. No. 17/176,450 filed Feb. 16, 2021, which is a continuation application of U.S. application Ser. No. 16/452,719 filed Jun. 26, 2019, which is a continuation of U.S. application Ser. No. 13/912,599, filed Jun. 7, 2013, which is a continuation application of U.S. application Ser. No. 12/703,988, filed Feb. 11, 2010, which claims benefit from U.S. Provisional Application No. 61/152,302, filed on Feb. 13, 2009, the content of which is incorporated herein in its entirety.

TECHNICAL FIELD OF THE INVENTION

The invention relates to a pharmaceutical composition comprising an SGLT2-inhibitor, a DPPIV inhibitor and a third antidiabetic agent selected from the group G3 as described hereinafter which is suitable in the treatment or prevention of one or more conditions selected from type 1 diabetes mellitus, type 2 diabetes mellitus, impaired glucose tolerance, impaired fasting blood glucose and hyperglycemia inter alia.

Furthermore the invention relates to methods
for preventing, slowing progression of, delaying, or treating a metabolic disorder;
for improving glycemic control and/or for reducing of fasting plasma glucose, of postprandial plasma glucose and/or of glycosylated hemoglobin HbA1c;
for preventing, slowing, delaying or reversing progression from impaired glucose tolerance, impaired fasting blood glucose, insulin resistance and/or from metabolic syndrome to type 2 diabetes mellitus;
for preventing, slowing progression of, delaying or treating of a condition or disorder selected from the group consisting of complications of diabetes mellitus;
for reducing body weight and/or body fat or preventing an increase in body weight and/or body fat or facilitating a reduction in body weight and/or body fat;
for preventing or treating the degeneration of pancreatic beta cells and/or for improving and/or restoring the functionality of pancreatic beta cells and/or restoring the functionality of pancreatic insulin secretion;
for preventing, slowing, delaying or treating diseases or conditions attributed to an abnormal accumulation of ectopic fat;
maintaining and/or improving the insulin sensitivity and/or for treating or preventing hyperinsulinemia and/or insulin resistance,
for preventing, slowing progression of, delaying, or treating new onset diabetes after transplantation (NODAT) and/or post-transplant metabolic syndrome (PTMS);
for preventing, delaying, or reducing NODAT and/or PTMS associated complications including micro- and macrovascular diseases and events, graft rejection, infection, and death;
for treating hyperuricemia and hyperuricemia associated conditions;
for treating or preventing kidney stones;
for treating hyponatremia;
in patients in need thereof characterized in that an SGLT2 inhibitor, a DPPIV inhibitor and optionally a third antidiabetic agent as defined hereinafter is administered in combination or alternation.

In addition the present invention relates to the use of an SGLT2 inhibitor for the manufacture of a medicament for use in a method as described hereinbefore and hereinafter.

In addition, the present invention relates to the use of a DPP IV inhibitor for the manufacture of a medicament for use in a method as described hereinbefore and hereinafter.

In addition, the present invention relates to the use of a third antidiabetic agent as defined hereinafter for the manufacture of a medicament for use in a method as described hereinbefore and hereinafter.

The invention also relates to a use of a pharmaceutical composition according to this invention for the manufacture of a medicament for use in a method as described hereinbefore and hereinafter.

BACKGROUND OF THE INVENTION

Type 2 diabetes is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

After long duration of disease, most patients with type 2 diabetes will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of n-cell function. Importantly, intensive treatment was not associated with a significant reduction in macrovascular complications, i.e. cardiovascular events. Therefore many patients with type 2 diabetes remain inadequately treated, partly because of limitations in long term efficacy, tolerability and dosing inconvenience of existing antihyperglycemic therapies.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

The high incidence of therapeutic failure is a major contributor to the high rate of long-term hyperglycemia-associated complications or chronic damages (including micro- and macrovascular complications such as e.g. diabetic nephropathy, retinopathy or neuropathy, or cardiovascular complications) in patients with type 2 diabetes.

Therefore, there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

SGLT2 inhibitors represent a novel class of agents that are being developed for the treatment or improvement in glycemic control in patients with type 2 diabetes. Glucopyranosyl-substituted benzene derivative are described in the prior art as SGLT2 inhibitors, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient. There are at least 3 SGLT isoforms that differ in their expression pattern as well as in their physico-chemical properties. SGLT2 is exclusively expressed in the kidney, whereas SGLT1 is expressed additionally in other tissues like intestine, colon, skeletal and cardiac muscle. SGLT3 has been found to be a glucose sensor in interstitial cells of the intestine without any transport function. Potentially, other related, but not yet characterized genes, may contribute further to renal glucose reuptake. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentrations and to glucosuria.

DPP IV inhibitors represent another novel class of agents that are being developed for the treatment or improvement in glycemic control in patients with type 2 diabetes.

For example, DPP IV inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/054201, WO 2007/128721 or WO 2007/128761.

AIM OF THE PRESENT INVENTION

The aim of the present invention is to provide a pharmaceutical composition and method for preventing, slowing progression of, delaying or treating a metabolic disorder, in particular of type 2 diabetes mellitus.

A further aim of the present invention is to provide a pharmaceutical composition and method for improving glycemic control in a patient in need thereof, in particular in patients with type 2 diabetes mellitus.

Another aim of the present invention is to provide a pharmaceutical composition and method for improving glycemic control in a patient with insufficient glycemic control despite monotherapy with an antidiabetic drug, for example metformin, or despite combination therapy with two antidiabetic drugs.

Another aim of the present invention is to provide a pharmaceutical composition and method for preventing, slowing or delaying progression from impaired glucose tolerance (IGT), impaired fasting blood glucose (IFG), insulin resistance and/or metabolic syndrome to type 2 diabetes mellitus.

Yet another aim of the present invention is to provide a pharmaceutical composition and method for preventing, slowing progression of, delaying or treating of a condition or disorder from the group consisting of complications of diabetes mellitus.

A further aim of the present invention is to provide a pharmaceutical composition and method for reducing the weight or preventing an increase of the weight in a patient in need thereof.

Another aim of the present invention is to provide a new pharmaceutical composition with a high efficacy for the treatment of metabolic disorders, in particular of diabetes mellitus, impaired glucose tolerance (IGT), impaired fasting blood glucose (IFG), and/or hyperglycemia, which has good to very good pharmacological and/or pharmacokinetic and/or physicochemical properties.

Further aims of the present invention become apparent to the one skilled in the art by description hereinbefore and in the following and by the examples.

SUMMARY OF THE INVENTION

Within the scope of the present invention it has now surprisingly been found that a pharmaceutical composition comprising a SGLT2 inhibitor and a DPP IV inhibitor and a third antidiabetic agent selected from the group G3 as defined hereinafter can advantageously be used for preventing, slowing progression of, delaying or treating a metabolic disorder, in particular for improving glycemic control in patients. This opens up new therapeutic possibilities in the treatment and prevention of type 2 diabetes mellitus, overweight, obesity, complications of diabetes mellitus and of neighboring disease states.

Therefore, in a first aspect the present invention provides a pharmaceutical composition comprising
  (a) an SGLT2 inhibitor, and
  (b) a DPPIV inhibitor, and
  (c) a third antidiabetic agent selected from the group G3 consisting of biguanides, thiazolidindiones, sulfonylureas, glinides, inhibitors of alpha-glucosidase, GLP-1 analogues or a pharmaceutically acceptable salt thereof.

According to another aspect of the invention, there is provided a method for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity, metabolic syndrome and gestational diabetes in a patient in need thereof characterized in that an SGLT2 inhibitor, a DPPIV inhibitor and optionally a third antidiabetic agent as defined hereinbefore and hereinafter are administered, for example in combination or alternation, to the patient.

According to another aspect of the invention, there is provided a method for improving glycemic control and/or for reducing of fasting plasma glucose, of postprandial plasma glucose and/or of glycosylated hemoglobin HbA1c in a patient in need thereof characterized in that an SGLT2 inhibitor, a DPPIV inhibitor and optionally a third antidiabetic agent as defined hereinbefore and hereinafter are administered, for example in combination or alternation, to the patient.

The pharmaceutical composition according to this invention may also have valuable disease-modifying properties with respect to diseases or conditions related to impaired glucose tolerance (IGT), impaired fasting blood glucose (IFG), insulin resistance and/or metabolic syndrome.

According to another aspect of the invention, there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that an SGLT2 inhibitor, a DPPIV inhibitor and optionally a third antidiabetic agent as defined hereinbefore and hereinafter are administered, for example in combination or alternation, to the patient.

As by the use of a pharmaceutical composition according to this invention, an improvement of the glycemic control in patients in need thereof is obtainable, also those conditions and/or diseases related to or caused by an increased blood glucose level may be treated.

According to another aspect of the invention, there is provided a method for preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis, in a patient in need thereof characterized in that an SGLT2 inhibitor, a DPPIV inhibitor and optionally a third antidiabetic agent as defined hereinbefore and hereinafter are administered, for example in combination or alternation, to the patient. In particular one or more aspects of diabetic nephropathy such as hyperperfusion, proteinuria and albuminuria may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

By the administration of a pharmaceutical composition according to this invention and due to the activity of the SGLT2 inhibitor excessive blood glucose levels are not converted to insoluble storage forms, like fat, but excreted through the urine of the patient. In animal models using a SGLT2 inhibitor it can be seen that loss of fat accounts for the majority of the observed weight loss whereas no significant changes in body water or protein content are observed. Therefore, no gain in weight or even a reduction in body weight is the result.

According to another aspect of the invention, there is provided a method for reducing body weight and/or body fat or preventing an increase in body weight and/or body fat or facilitating a reduction in body weight and/or body fat in a patient in need thereof characterized in that an SGLT2 inhibitor, a DPPIV inhibitor and optionally a third antidiabetic agent as defined hereinbefore and hereinafter are administered, for example in combination or alternation, to the patient.

The pharmacological effect of the SGLT2 inhibitor in the pharmaceutical composition according to this invention is independent of insulin. Therefore, an improvement of the glycemic control is possible without an additional strain on the pancreatic beta cells. By an administration of a pharmaceutical composition according to this invention a beta-cell degeneration and a decline of beta-cell functionality such as for example apoptosis or necrosis of pancreatic beta cells can be delayed or prevented. Furthermore, the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition according to this invention.

According to another aspect of the invention, there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof characterized in that an SGLT2 inhibitor, a DPPIV inhibitor and optionally a third antidiabetic agent as defined hereinbefore and hereinafter are administered, for example in combination or alternation, to the patient.

By the administration of a combination or pharmaceutical composition according to the present invention, an abnormal accumulation of ectopic fat, in particular of the liver, may be reduced or inhibited. Therefore, according to another aspect of the present invention, there is provided a method for preventing, slowing, delaying or treating diseases or conditions attributed to an abnormal accumulation of ectopic fat, in particular of the liver, in a patient in need thereof characterized in that an SGLT2 inhibitor, a DPPIV inhibitor and optionally a third antidiabetic agent as defined hereinbefore and hereinafter are administered, for example in combination or alternation, to the patient. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

As a result thereof, another aspect of the invention provides a method for maintaining and/or improving the insulin sensitivity and/or for treating or preventing hyperinsulinemia and/or insulin resistance in a patient in need thereof characterized in that an SGLT2 inhibitor, a DPPIV inhibitor and optionally a third antidiabetic agent as defined hereinbefore and hereinafter are administered, for example in combination or alternation, to the patient.

According to another aspect of the invention, there is provided a method for preventing, slowing progression of, delaying, or treating new onset diabetes after transplantation (NODAT) and/or post-transplant metabolic syndrome (PTMS) in a patient in need thereof characterized in that an SGLT2 inhibitor, a DPPIV inhibitor and optionally a third antidiabetic agent as defined hereinbefore and hereinafter are administered, for example in combination or alternation, to the patient.

According to a further aspect of the invention, there is provided a method for preventing, delaying, or reducing NODAT and/or PTMS associated complications including micro- and macrovascular diseases and events, graft rejection, infection, and death in a patient in need thereof characterized in that an SGLT2 inhibitor, a DPPIV inhibitor and optionally a third antidiabetic agent as defined hereinbefore and hereinafter are administered, for example in combination or alternation, to the patient.

The pharmaceutical composition according to the invention is capable of facilitating the lowering of serum total urate levels in the patient. Therefore according to another aspect of the invention, there is provided a method for treating hyperuricemia and hyperuricemia-associated conditions, such as for example gout, hypertension and renal failure, in a patient in need thereof characterized in that an SGLT2 inhibitor, a DPPIV inhibitor and optionally a third antidiabetic agent as defined hereinbefore and hereinafter are administered, for example in combination or alternation, to the patient. The patient may be a diabetic or non-diabetic patient.

The administration of a pharmaceutical composition increases the urine excretion of glucose. This increase in osmotic excretion and water release and the lowering of urate levels are beneficial as a treatment or prevention for kidney stones. Therefore in a further aspect of the invention, there is provided a method for treating or preventing kidney stones in a patient in need thereof characterized in that an SGLT2 inhibitor, a DPPIV inhibitor and optionally a third antidiabetic agent as defined hereinbefore and hereinafter are administered, for example in combination or alternation, to the patient.

According to a further aspect of the invention, there is provided a method for treating hyponatremia, water retention and water intoxication in a patient in need thereof characterized in that an SGLT2 inhibitor, a DPPIV inhibitor and optionally a third antidiabetic agent as defined hereinbefore and hereinafter are administered, for example in combination or alternation, to the patient. By the administration of the pharmaceutical composition according to this invention it may be possible to reverse the effects of hyponatremia, water retention and water intoxication by acting on the kidney to reverse water retention and electrolyte imbalances associated with these diseases and disorders.

According to another aspect of the invention there is provided the use of an SGLT2 inhibitor for the manufacture of a medicament for
  preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity, metabolic syndrome and gestational diabetes; or
  improving glycemic control and/or for reducing of fasting plasma glucose, of postprandial plasma glucose and/or of glycosylated hemoglobin HbA1c; or
  preventing, slowing, delaying or reversing progression from impaired glucose tolerance (IGT), impaired fasting blood glucose (IFG), insulin resistance and/or from metabolic syndrome to type 2 diabetes mellitus; or
  preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or
  reducing body weight and/or body fat or preventing an increase in body weight and/or body fat or facilitating a reduction in body weight and/or body fat; or
  preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or
  preventing, slowing, delaying or treating diseases or conditions attributed to an abnormal accumulation of ectopic fat; or
  maintaining and/or improving the insulin sensitivity and/or for treating or preventing hyperinsulinemia and/or insulin resistance;
  preventing, slowing progression of, delaying, or treating new onset diabetes after transplantation (NODAT) and/or post-transplant metabolic syndrome (PTMS);
  preventing, delaying, or reducing NODAT and/or PTMS associated complications including micro- and macrovascular diseases and events, graft rejection, infection, and death;
  treating hyperuricemia and hyperuricemia associated conditions;
  treating or prevention kidney stones;
  treating hyponatremia;
in a patient in need thereof characterized in that the SGLT2 inhibitor is administered, for example in combination or alternation, with a DPP IV inhibitor and optionally a third antidiabetic agent as defined hereinbefore and hereinafter.

According to another aspect of the invention, there is provided the use of a DPP IV inhibitor as defined hereinbefore and hereinafter for the manufacture of a medicament for
  preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or
  improving glycemic control and/or for reducing of fasting plasma glucose, of postprandial plasma glucose and/or of glycosylated hemoglobin HbA1c; or
  preventing, slowing, delaying or reversing progression from impaired glucose tolerance (IGT), impaired fasting blood glucose (IFG), insulin resistance and/or from metabolic syndrome to type 2 diabetes mellitus; or
  preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or
  reducing body weight and/or body fat or preventing an increase in body weight and/or body fat or facilitating a reduction in body weight and/or body fat; or
  preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or
  preventing, slowing, delaying or treating diseases or conditions attributed to an abnormal accumulation of liver fat; or
  maintaining and/or improving the insulin sensitivity and/or for treating or preventing hyperinsulinemia and/or insulin resistance;
in a patient in need thereof characterized in that the DPP IV inhibitor is administered, for example in combination or alternation, with an SGLT2 inhibitor and optionally a third antidiabetic agent as defined hereinbefore and hereinafter.

According to another aspect of the invention, there is provided the use of a third antidiabetic agent as defined hereinbefore and hereinafter for the manufacture of a medicament for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, arteriosclerosis, myocardial infarction, stroke and peripheral arterial occlusive disease; or reducing body weight and/or body fat or preventing an increase in body weight and/or body fat or facilitating a reduction in body weight and/or body fat; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance;

in a patient in need thereof characterized in that the third antidiabetic agent is administered, for example in combination or alternation, with an SGLT2 inhibitor and a DPPIV inhibitor as defined hereinbefore and hereinafter.

According to another aspect of the invention, there is provided the use of a pharmaceutical composition according to the present invention for the manufacture of a medicament for a therapeutic and preventive method as described hereinbefore and hereinafter.

Definitions

The term "active ingredient" of a pharmaceutical composition according to the present invention means the SGLT2 inhibitor and/or the DPP IV inhibitor according to the present invention.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dL (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28: 412-19), of the ratio of intact proinsulin to insulin (Forst et al., *Diabetes* 2003, 52 (Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

HOMA-IR=[fasting serum insulin (µU/mL)]×[fasting plasma glucose(mmol/L)/22.5]

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28: 412-19), the ratio of intact proinsulin to insulin (Forst et al., *Diabetes* 2003, 52 (Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference 85 cm in men and 90 cm in women;
2. Triglycerides: ≥150 mg/dL
3. HDL-cholesterol <40 mg/dL in men
4. Blood pressure ≥130/85 mm Hg (SBP≥130 or DBP≥85)
5. Fasting blood glucose ≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The definitions of NODAT (new onset diabetes after transplantation) and PTMS (post-transplant metabolic syndrome) follow closely that of the American Diabetes Association diagnostic criteria for type 2 diabetes, and that of the International Diabetes Federation (IDF) and the American Heart Association/National Heart, Lung, and Blood Institute, for the metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pretransplant body mass index, pre-transplant diabetes, and immunosuppression.

The term "gestational diabetes" (diabetes of pregnancy) denotes a form of the diabetes which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test, for example with 75 g of glucose.

The term "hyperuricemia" denotes a condition of high serum total urate levels. In human blood, uric acid concentrations between 3.6 mg/dL (ca. 214 μmol/L) and 8.3 mg/dL (ca. 494 μmol/L) are considered normal by the American Medical Association. High serum total urate levels, or hyperuricemia, are often associated with several maladies. For example, high serum total urate levels can lead to a type of arthritis in the joints known as gout. Gout is a condition created by a build up of monosodium urate or uric acid crystals on the articular cartilage of joints, tendons and surrounding tissues due to elevated concentrations of total urate levels in the blood stream. The build up of urate or uric acid on these tissues provokes an inflammatory reaction of these tissues. Saturation levels of uric acid in urine may result in kidney stone formation when the uric acid or urate crystallizes in the kidney. Additionally, high serum total urate levels are often associated with the so-called metabolic syndrome, including cardiovascular disease and hypertension.

The term "hyponatremia" denotes a condition of a positive balance of water with or without a deficit of sodium, which is recognized when the plasma sodium falls below the level of 135 mml/L. Hyponatremia is a condition which can occur in isolation in individuals that over-consume water; however, more often hyponatremia is a complication of medication or other underlying medical condition that leas to a diminished excretion of water. Hyponatremia may lead to water intoxication, which occurs when the normal tonicity of extracellular fluid falls below the safe limit, due to retention of excess water. Water intoxication is a potentially fatal disturbance in brain function. Typical symptoms of water intoxication include nausea, vomiting, headache and malaise.

The term "SGLT2 inhibitor" in the scope of the present invention relates to a compound, in particular to a glucopyranosyl-derivative, i.e. compound having a glucopyranosyl-moiety, which shows an inhibitory effect on the sodium-glucose transporter 2 (SGLT2), in particular the human SGLT2. The inhibitory effect on hSGLT2 measured as 1050 is preferably below 1000 nM, even more preferably below 100 nM, most preferably below 50 nM. IC50 values of SGLT2 inhibitors are usually above 0.01 nM, or even equal to or above 0.1 nM. The inhibitory effect on hSGLT2 can be determined by methods known in the literature, in particular as described in the application WO 2005/092877 or WO 2007/093610 (pages 23/24), which are incorporated herein by reference in its entirety. The term "SGLT2 inhibitor" also comprises any pharmaceutically acceptable salts thereof, hydrates and solvates thereof, including the respective crystalline forms.

The term "DPPIV inhibitor" in the scope of the present invention relates to a compound that exhibits inhibitory activity on the enzyme dipeptidyl peptidase IV. Such inhibitory activity can be characterised by the 1050 value. A DPPIV inhibitor preferably exhibits an IC50 value below 10000 nM, preferably below 1000 nM. Certain DPPIV inhibitors exhibit an 1050 value below 100 nM, or even ≤50 nM. 1050 values of DPPIV inhibitors are usually above 0.01 nM, or even above 0.1 nM. DPPIV inhibitors may include biologic and non-biologic, in particular non-peptidic compounds. The inhibitory effect on DPPIV can be determined by methods known in the literature, in particular as described in the application WO 02/068420 or WO 2004/018468 (page 34), which are incorporated herein by reference in its entirety. The term "DPPIV inhibitor" also comprises any pharmaceutically acceptable salts thereof, hydrates and solvates thereof, including the respective crystalline forms.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventively treating" and "preventing" are used interchangeably and comprise a treatment of patients at risk to develop a condition mentioned hereinbefore, thus reducing said risk.

BRIEF DESCRIPTION OF THE FIGURES

The FIG. 1 shows the glucose excursion as glucose AUC in Zucker rats to which an SGLT2 inhibitor (A), a DPPIV inhibitor (B), metformin (Met) and combinations thereof (A+Met, B+Met, A+B, A+B+Met) were administered. Compound A is the glucopyranosyl-substituted benzene derivative (I.9), compound B is linagliptin.

DETAILED DESCRIPTION

The aspects according to the present invention, in particular the pharmaceutical compositions, methods and uses, refer to SGLT2 inhibitors, DPPIV inhibitors and third antidiabetic agents as defined hereinbefore and hereinafter. In the methods and uses according to this invention a third antidiabetic agent is optionally administered, i.e. the SGLT2 inhibitor and the DPPIV inhibitor are administered in combination with a third antidiabetic agent or without a third antidiabetic agent. Preferably in the methods and uses according to this invention the SGLT2 inhibitor and the DPPIV inhibitor are administered in combination with a third antidiabetic agent.

Preferably the SGLT2 inhibitor is selected from the group G1 consisting of dapagliflozin, canagliflozin, atigliflozin, remogliflozin, sergliflozin and glucopyranosyl-substituted benzene derivatives of the formula (I)

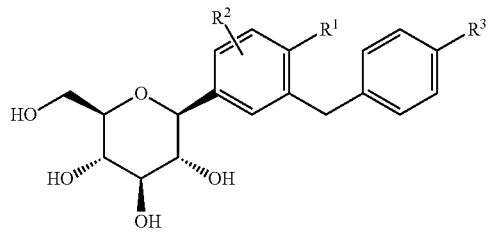

wherein $R^1$ denotes Cl, methyl or cyano; $R^2$ denotes H, methyl, methoxy or hydroxy and $R^3$ denotes ethyl, cyclopropyl, ethynyl, ethoxy, (R)-tetrahydrofuran-3-yloxy or (S)-tetrahydrofuran-3-yloxy; or a prodrug of one of the beforementioned SGLT2 inhibitors.

Compounds of the formula (I) and methods of their synthesis are described for example in the following patent applications: WO 2005/092877, WO 2006/117360, WO 2006/117359, WO 2006/120208, WO 2006/064033, WO 2007/031548, WO 2007/093610, WO 2008/020011, WO 2008/055870.

In the above glucopyranosyl-substituted benzene derivatives of the formula (I) the following definitions of the substituents are preferred.

Preferably $R^1$ denotes chloro or cyano; in particular chloro.

Preferably $R^2$ denotes H.

Preferably $R^3$ denotes ethyl, cyclopropyl, ethynyl, (R)-tetrahydrofuran-3-yloxy or (S)-tetrahydrofuran-3-yloxy. Even more preferably $R^3$ denotes cyclopropyl, ethynyl, (R)-tetrahydrofuran-3-yloxy or (S)-tetrahydrofuran-3-yloxy.

Most preferably $R^3$ denotes ethynyl, (R)-tetrahydrofuran-3-yloxy or (S)-tetrahydrofuran-3-yloxy.

Preferred glucopyranosyl-substituted benzene derivatives of the formula (I) are selected from the group of compounds (I.1) to (I.11):

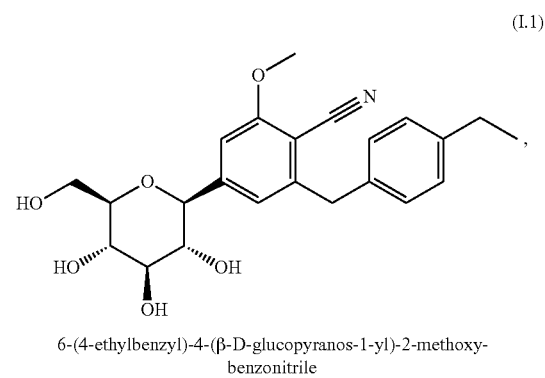

6-(4-ethylbenzyl)-4-(β-D-glucopyranos-1-yl)-2-methoxybenzonitrile

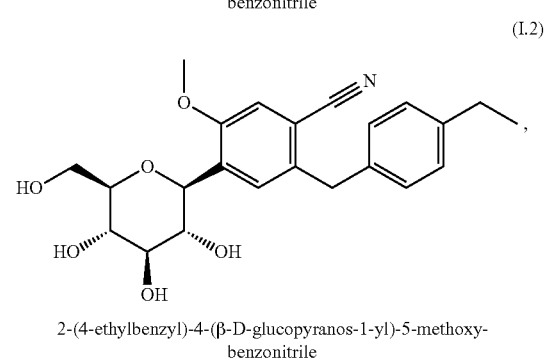

2-(4-ethylbenzyl)-4-(β-D-glucopyranos-1-yl)-5-methoxybenzonitrile

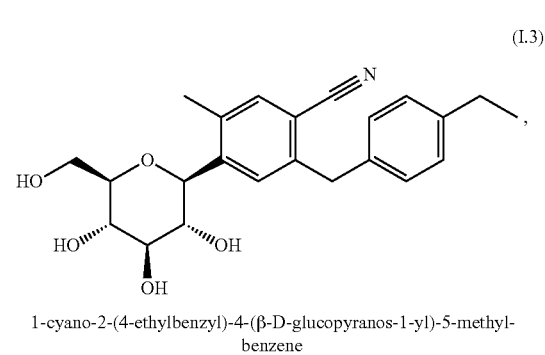

1-cyano-2-(4-ethylbenzyl)-4-(β-D-glucopyranos-1-yl)-5-methylbenzene

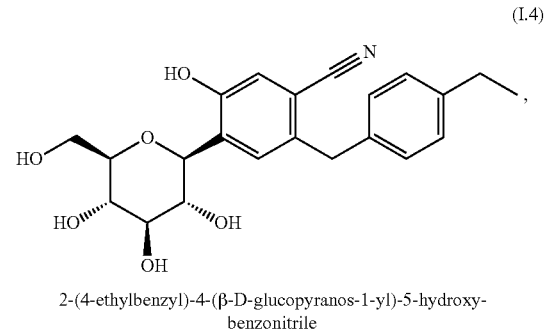

2-(4-ethylbenzyl)-4-(β-D-glucopyranos-1-yl)-5-hydroxybenzonitrile

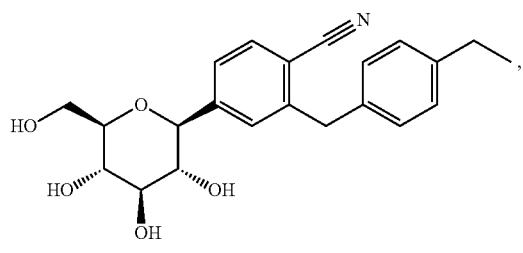

2-(4-ethyl-benzyl)-4-(β-D-glucopyranos-1-yl)-benzonitrile (I.5)

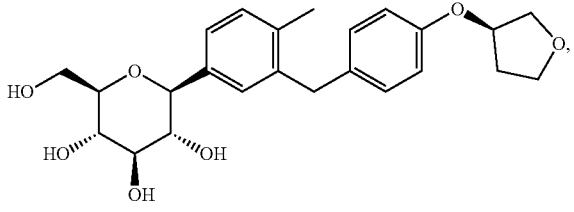

1-methyl-2-[4-((R)-tetrahydrofuran-3-yloxy)-benzyl]-4-(β-D-glucopyranos-1-yl)-benzene (I.10)

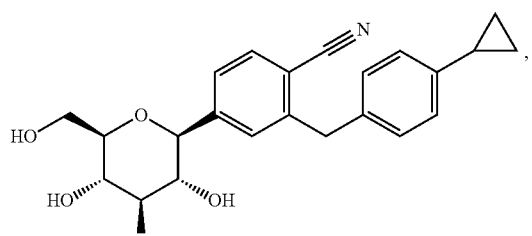

2-(4-cyclopropyl-benzyl)-4-(β-D-glucopyranos-1-yl)-benzonitrile (I.6)

1-methyl-2-[4-((S)-tetrahydrofuran-3-yloxy)-benzyl]-4-(β-D-glucopyranos-1-yl)-benzene (I.11)

Even more preferred glucopyranosyl-substituted benzene derivatives of the formula (I) are selected from the compounds (I.6), (I.7), (I.8), (I.9) and (I.11).

Therefore the group G1 preferably consists of dapagliflozin, remogliflozin, the compound (I.6), the compound (I.7), the compound (I.8), the compound (I.9) and the compound (I.11).

Even more preferably the group G1 consists of dapagliflozin and the compound (I.9).

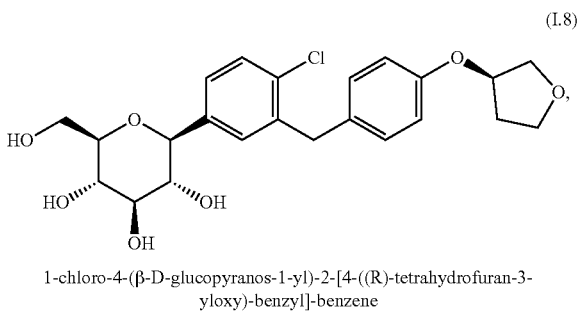

1-chloro-(4-(β-D-glucopyranos-1-yl)-2-(4-ethynyl-benzyl)-benzene (I.7)

According to this invention, it is to be understood that the definitions of the above listed glucopyranosyl-substituted benzene derivatives of the formula (I) also comprise their hydrates, solvates and polymorphic forms thereof, and prodrugs thereof. With regard to the preferred compound (I.7) an advantageous crystalline form is described in the international patent application WO 2007/028814 which hereby is incorporated herein in its entirety. With regard to the preferred compound (I.8), an advantageous crystalline form is described in the international patent application WO 2006/117360 which hereby is incorporated herein in its entirety. With regard to the preferred compound (I.9) an advantageous crystalline form is described in the international patent application WO 2006/117359 which hereby is incorporated herein in its entirety. With regard to the preferred compound (I.11) an advantageous crystalline form is described in the international patent application WO 2008/049923 which hereby is incorporated herein in its entirety. These crystalline forms possess good solubility properties which enable a good bioavailability of the SGLT2 inhibitor. Furthermore, the crystalline forms are physico-chemically stable and thus provide a good shelf-life stability of the pharmaceutical composition.

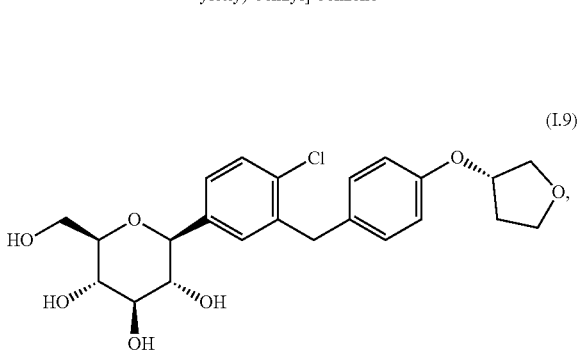

1-chloro-4-(β-D-glucopyranos-1-yl)-2-[4-((R)-tetrahydrofuran-3-yloxy)-benzyl]-benzene (I.8)

1-chloro-4-(β-D-glucopyranos-1-yl)-2-[4-((S)-tetrahydrofuran-3-yloxy)-benzyl]-benzene (I.9)

The term "dapagliflozin" as employed herein refers to dapagliflozin, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin, including hydrates and solvates thereof, and crystalline forms thereof and has the following structure:

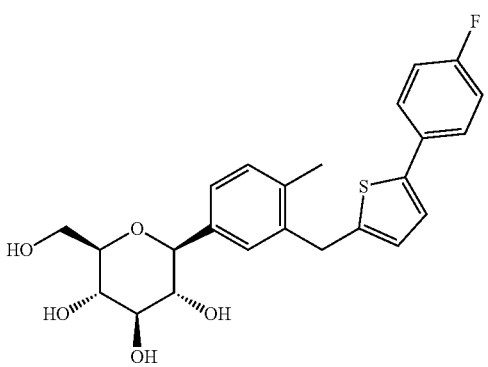 [SMILES: Cc1ccc([C@@H]2O[C@H](CO)[C@@H](O)[C@H](O)[C@H]2O)cc1Cc1ccc(-c2ccc(F)cc2)s1]

The compound and methods of its synthesis are described in WO 2005/012326 and WO 2009/035969 for example. Preferred hydrates, solvates and crystalline forms are described in the patent applications WO 2008/069327 for example.

The term "atigliflozin" as employed herein refers to atigliflozin, including hydrates and solvates thereof, and crystalline forms thereof. The compound and methods of its synthesis are described in WO 2004/007517 for example.

The term "remogliflozin" as employed herein refers to remogliflozin and prodrugs of remogliflozin, in particular remogliflozin etabonate, including hydrates and solvates thereof, and crystalline forms thereof. Methods of its synthesis are described in the patent applications EP 1213296 and EP 1354888 for example.

The term "sergliflozin" as employed herein refers to sergliflozin and prodrugs of sergliflozin, in particular sergliflozin etabonate, including hydrates and solvates thereof, and crystalline forms thereof. Methods for its manufacture are described in the patent applications EP 1344780 and EP 1489089 for example.

For avoidance of any doubt, the disclosure of each of the foregoing documents cited above in connection with the specified SGLT2 inhibitors is specifically incorporated herein by reference in its entirety.

The aspects according to the present invention, in particular the pharmaceutical compositions, methods and uses, refer to a DPP IV inhibitor as defined hereinbefore and hereinafter, or prodrugs thereof, or pharmaceutically acceptable salts thereof.

Preferably the DPPIV inhibitor is selected from the group G2 consisting of linagliptin, sitagliptin, vildagliptin, alogliptin, saxagliptin, denagliptin, carmegliptin, melogliptin and dutogliptin, or a pharmaceutically acceptable salt of one of the beforementioned DPPIV inhibitors, or a prodrug thereof.

The term "linagliptin" as employed herein refers to linagliptin and pharmaceutically acceptable salts thereof, including hydrates and solvates thereof, and crystalline forms thereof. Crystalline forms are described in WO 2007/128721. Methods for the manufacture of linagliptin are described in the patent applications WO 2004/018468 and WO 2006/048427 for example. Linagliptin is distinguished from structurally comparable DPP IV inhibitors, as it combines exceptional potency and a long-lasting effect with favourable pharmacological properties, receptor selectivity and a favourable side-effect profile or bring about unexpected therapeutic advantages or improvements when used in combination with an SGLT2 inhibitor and a third antidiabetic agent according to this invention.

The term "sitagliptin" as employed herein refers to sitagliptin (or MK-0431) and pharmaceutically acceptable salts thereof, including hydrates and solvates thereof, and crystalline forms thereof. In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485. For details, e.g. on a process to manufacture or to formulate this compound or a salt thereof, reference is thus made to these documents. A tablet formulation for sitagliptin is commercially available under the trade name Januvia®.

The term "vildagliptin" as employed herein refers to vildagliptin (or LAF-237) and pharmaceutically acceptable salts thereof, including hydrates and solvates thereof, and crystalline forms thereof. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723. For details, e.g. on a process to manufacture or to formulate this compound or a salt thereof, reference is thus made to these documents and U.S. Pat. No. 6,166,063. A tablet formulation for vildagliptin is expected to be commercially available under the trade name Galvus®.

The term "saxagliptin" as employed herein refers to saxagliptin (or BMS-477118) and pharmaceutically acceptable salts thereof, including hydrates and solvates thereof, and crystalline forms thereof. In one embodiment, saxagliptin is in the form of the free base or a HCl salt (for example as mono- or dihydrochloride, including hydrates thereof), or a mono-benzoate salt as disclosed in WO 2004/052850 and WO 2008/131149. In a further embodiment, saxagliptin is in the form of the free base. In a yet further embodiment, saxagliptin is in the form of the monohydrate of the free base as disclosed in WO 2004/052850. A process for preparing saxagliptin is also disclosed in WO 2005/106011 and WO 2005/115982. Saxagliptin can be formulated in a tablet as described in WO 2005/117841. For details, e.g. on a process to manufacture, to formulate or to use this compound or a salt thereof, reference is thus made to these documents and U.S. Pat. No. 6,395,767 and WO 01/68603.

The term "denagliptin" as employed herein refers to denagliptin (or GSK-823093) and pharmaceutically acceptable salts thereof, including hydrates and solvates thereof, and crystalline forms thereof. In one embodiment, denagliptin is in the form of its hydrochloride salt as disclosed in Example 2 of WO 03/002531 or its tosylate salt as disclosed in WO 2005/009956. A class of this embodiment refers to denagliptin tosylate. Crystalline anhydrous denagliptin tosylate is disclosed in WO 2005/009956. For details on a process to manufacture this compound or a salt thereof, reference is thus made to these documents and to the U.S. Pat. No. 7,132,443.

The term "alogliptin" as employed herein refers to alogliptin (or SYR-322) and pharmaceutically acceptable salts thereof, including hydrates and solvates thereof, and crystalline forms thereof. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/

112368 and, specifically, in WO 2007/035629. Alogliptin (namely its benzoate salt) can be formulated in a tablet and administered as described in WO 2007/033266. For details, e.g. on a process to manufacture, to formulate or to use this compound or a salt thereof, reference is thus made to these documents and to US 2005/261271, EP 1586571 and WO 2005/095381.

The term "carmegliptin" as employed herein refers to carmegliptin and pharmaceutically acceptable salts thereof, including hydrates and solvates thereof, and crystalline forms thereof. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423. For details, e.g. on a process to manufacture, to formulate or to use this compound or a salt thereof, reference is thus made to these documents and to WO 2005/000848.

The term "melogliptin" as employed herein refers to melogliptin and pharmaceutically acceptable salts thereof, including hydrates and solvates thereof, and crystalline forms thereof. Methods for its preparation are inter alia disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

The term "dutogliptin" as employed herein refers to dutogliptin (or PHX-1149, PHX-1149T) and pharmaceutically acceptable salts thereof, including hydrates and solvates thereof, and crystalline forms thereof. Methods for its preparation are inter alia disclosed in WO 2005/047297. Pharmaceutically acceptable salts include the tartrate. For details, e.g. on a process to manufacture, to formulate or to use this compound or a salt thereof, reference is thus made to these documents.

For avoidance of any doubt, the disclosure of each of the foregoing documents cited above in connection with the specified DPP IV inhibitors is specifically incorporated herein by reference in its entirety.

The third antidiabetic agent is selected from the group G3 consisting of biguanides, thiazolidindiones, sulfonylureas, glinides, inhibitors of alpha-glucosidase, GLP-1 analogues or a pharmaceutically acceptable salt thereof. In the following preferred embodiments regarding the third antidiabetic agent are described.

The group G3 comprises biguanides. Examples of biguanides are metformin, phenformin and buformin. A preferred biguanide is metformin. An SGLT2 inhibitor and a DPPIV inhibitor in combination with a biguanide, in particular metformin, can provide more efficacious glycemic control and may act synergistically with the biguanide, for example to reduce weight that has overall beneficial effects on the metabolic syndrome which is commonly associated with type 2 diabetes mellitus.

The term "metformin" as employed herein refers to metformin or a pharmaceutically acceptable salt thereof such as the hydrochloride salt, the metformin (2:1) fumarate salt, and the metformin (2:1) succinate salt, the hydrobromide salt, the p-chlorophenoxy acetate or the embonate, and other known metformin salts of mono and dibasic carboxylic acids. It is preferred that the metformin employed herein is the metformin hydrochloride salt.

The group G3 comprises thiazolidindiones. Examples of thiazolidindiones (TZD) are pioglitazone and rosiglitazone. TZD therapy is associated with massive weight gain and fat redistribution. In addition, TZD cause fluid retention and are not indicated in patients with congestive heart failure. Long term treatment with TZD are further associated with an increased risk of bone fractures. The advantageous properties, like the weight reducing capability, of a SGLT2 inhibitor and a DPPIV inhibitor can minimize side effects of the treatment with TZD.

The term "pioglitazone" as employed herein refers to pioglitazone, including its enantiomers, mixtures thereof and its racemate, or a pharmaceutically acceptable salt thereof such as the hydrochloride salt.

The term "rosiglitazone" as employed herein refers to rosiglitazone, including its enantiomers, mixtures thereof and its racemate, or a pharmaceutically acceptable salt thereof such as the maleate salt.

The group G3 comprises sulfonylureas. Examples of sulfonylureas are glibenclamide, tolbutamide, glimepiride, glipizide, gliquidone, glibornuride, glyburide, glisoxepide and gliclazide. Preferred sulfonylureas are tolbutamide, gliquidone, glibenclamide and glimepiride, in particular glibenclamide and glimepiride. As the efficacy of sulfonylureas wears off over the course of treatment, a combination of an SGLT2 inhibitor and a DPPIV inhibitor with a sulfonylurea may offer additional benefit to the patient in terms of better glycemic control. Also, treatment with sulfonylureas is normally associated with gradual weight gain over the course of treatment and weight reducing capability of a SGLT2 inhibitor and a DPPIV inhibitor can minimize this side effect of the treatment with an sulfonylurea and improve the metabolic syndrome. This combination may also allow a reduction in the dose of sulfonylureas which may translate into less hypoglycemia which is an undesirable side effect of sulfonylureas.

Each term of the group "glibenclamide", "glimepiride", "gliquidone", "glibornuride", "gliclazide", "glisoxepide", "tolbutamide" and "glipizide" as employed herein refers to the respective active drug or a pharmaceutically acceptable salt thereof.

The group G3 comprises glinides. Examples of glinides are nateglinide, repaglinide and mitiglinide. As their efficacy wears off over the course of treatment, a combination of a SGLT2 inhibitor with a meglitinide may offer additional benefit to the patient in terms of better glycemic control. Also, treatment with meglitinides is normally associated with gradual weight gain over the course of treatment and weight reducing capability of a SGLT2 inhibitor can minimize this side effect of the treatment with an meglitinide and improve the metabolic syndrome. This combination may also allow a reduction in the dose of meglitinides which may translate into less hypoglycemia which is an undesirable side effect of meglitinides.

The term "nateglinide" as employed herein refers to nateglinide, including its enantiomers, mixtures thereof and its racemate, or a pharmaceutically acceptable salts and esters thereof.

The term "repaglinide" as employed herein refers to repaglinide, including its enantiomers, mixtures thereof and its racemate, or a pharmaceutically acceptable salts and esters thereof.

The group G3 comprises inhibitors of alpha-glucosidase. Examples of inhibitors of alpha-glucosidase are acarbose, voglibose and miglitol. Additional benefits from the combination of an SGLT2 inhibitor, a DPPIV inhibitor and an alpha-glucosidase inhibitor may relate to more efficacious glycemic control at lower doses of the individual drugs, which in particular would reduce undesirable gastrointestinal side effects of alpha-glucosidase inhibitors. An additional benefit would be that the combination may result in higher systemic levels of systemic GLP-1 than the respective monotherapies with expected long-term benefits on pancreatic alpha- and beta-cells. Furthermore, combining both inhibition of glucose uptake in the intestine and increasing urinary excretion of blood glucose may lower blood glucose, in particular a postprandial glucose peak, much more efficiently than the respective monotherapies. Inhibitors of alpha-glucosidase are not absorbed or have exceedingly low systemic absorption and thus are expected not to interfere with the clearance of the DPPIV and the SGLT2 inhibitor.

Each term of the group "acarbose", "voglibose" and "miglitol" as employed herein refers to the respective active drug or a pharmaceutically acceptable salt thereof.

The group G3 comprises inhibitors of GLP-1 analogues. Examples of GLP-1 analogues are exenatide and liraglutide. The combination of an SGLT2 inhibitor, a DPPIV inhibitor and a GLP-1 analogue may achieve a superior glycemic control at lower doses of the individual drugs. In addition, the body weight reducing capability of the GLP-1 analogue is expected to be further enhanced by the potential for body weight control of the DPPIV inhibitor and the SGLT2 inhibitor. On the other hand, a reduction of side effects (e.g. nausea, vomiting) may be obtained, when a reduced dose of the GLP-1 analogue is applied in the combination with a DPP IV and a SGLT2 inhibitor.

Each term of the group "exenatide" and "liraglutide" as employed herein refers to the respective active drug or a pharmaceutically acceptable salt thereof.

In a first embodiment E1 the pharmaceutical compositions, methods and uses according to this invention preferably relate to combinations wherein the SGLT2 inhibitor is selected from glucopyranosyl-substituted benzene derivatives of the formula (I)

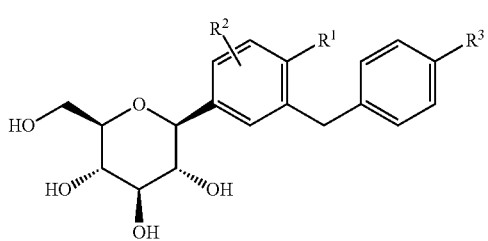

wherein $R^1$, $R^2$ and $R^3$ are defined as hereinbefore. Even more preferably the SGLT2 inhibitor is selected from group of compounds (I.1) to (I.11) as defined hereinbefore. Most preferably according to the first embodiment the SGLT2 inhibitor is the compound (I.9). According to the first embodiment the DPPIV inhibitor and the third antidiabetic agent are preferably selected according to the entries in the Table 1.

TABLE 1

| Embodiment | DPPIV Inhibitor | Third Antidiabetic Agent |
|---|---|---|
| E1.1 | selected from the group G2 | selected from the group G3 |
| E1.2 | selected from the group G2 | Metformin |
| E1.3 | selected from the group G2 | Pioglitazone |
| E1.4 | selected from the group G2 | Rosiglitazone |
| E1.5 | selected from the group G2 | Glibenclamide |
| E1.6 | selected from the group G2 | Glimepiride |
| E1.7 | selected from the group G2 | Gliquidone |
| E1.8 | selected from the group G2 | Nateglinide |

TABLE 1-continued

| Embodiment | DPPIV Inhibitor | Third Antidiabetic Agent |
|---|---|---|
| E1.9 | selected from the group G2 | Repaglinide |
| E1.10 | Linagliptin | selected from the group G3 |
| E1.11 | Linagliptin | Metformin |
| E1.12 | Linagliptin | Pioglitazone |
| E1.13 | Linagliptin | Rosiglitazone |
| E1.14 | Linagliptin | Glibenclamide |
| E1.15 | Linagliptin | Glimepiride |
| E1.16 | Linagliptin | Gliquidone |
| E1.17 | Linagliptin | Nateglinide |
| E1.18 | Linagliptin | Repaglinide |
| E1.19 | Sitagliptin | selected from the group G3 |
| E1.20 | Sitagliptin | Metformin |
| E1.21 | Sitagliptin | Pioglitazone |
| E1.22 | Sitagliptin | Rosiglitazone |
| E1.23 | Sitagliptin | Glibenclamide |
| E1.24 | Sitagliptin | Glimepiride |
| E1.25 | Sitagliptin | Gliquidone |
| E1.26 | Sitagliptin | Nateglinide |
| E1.27 | Sitagliptin | Repaglinide |
| E1.28 | Vildagliptin | selected from the group G3 |
| E1.29 | Vildagliptin | Metformin |
| E1.30 | Vildagliptin | Pioglitazone |
| E1.31 | Vildagliptin | Rosiglitazone |
| E1.32 | Vildagliptin | Glibenclamide |
| E1.33 | Vildagliptin | Glimepiride |
| E1.34 | Vildagliptin | Gliquidone |
| E1.35 | Vildagliptin | Nateglinide |
| E1.36 | Vildagliptin | Repaglinide |
| E1.37 | Alogliptin | selected from the group G3 |
| E1.38 | Alogliptin | Metformin |
| E1.39 | Alogliptin | Pioglitazone |
| E1.40 | Alogliptin | Rosiglitazone |
| E1.41 | Alogliptin | Glibenclamide |
| E1.42 | Alogliptin | Glimepiride |
| E1.43 | Alogliptin | Gliquidone |
| E1.44 | Alogliptin | Nateglinide |
| E1.45 | Alogliptin | Repaglinide |
| E1.46 | Saxagliptin | selected from the group G3 |
| E1.47 | Saxagliptin | Metformin |
| E1.48 | Saxagliptin | Pioglitazone |
| E1.49 | Saxagliptin | Rosiglitazone |
| E1.50 | Saxagliptin | Glibenclamide |
| E1.51 | Saxagliptin | Glimepiride |
| E1.52 | Saxagliptin | Gliquidone |
| E1.53 | Saxagliptin | Nateglinide |
| E1.54 | Saxagliptin | Repaglinide |
| E1.55 | Carmegliptin | selected from the group G3 |
| E1.56 | Carmegliptin | Metformin |
| E1.57 | Carmegliptin | Pioglitazone |
| E1.58 | Carmegliptin | Rosiglitazone |
| E1.59 | Carmegliptin | Glibenclamide |
| E1.60 | Carmegliptin | Glimepiride |
| E1.61 | Carmegliptin | Gliquidone |
| E1.62 | Carmegliptin | Nateglinide |
| E1.63 | Carmegliptin | Repaglinide |
| E1.64 | Melogliptin | selected from the group G3 |
| E1.65 | Melogliptin | Metformin |
| E1.66 | Melogliptin | Pioglitazone |
| E1.67 | Melogliptin | Rosiglitazone |
| E1.68 | Melogliptin | Glibenclamide |
| E1.69 | Melogliptin | Glimepiride |
| E1.70 | Melogliptin | Gliquidone |
| E1.71 | Melogliptin | Nateglinide |
| E1.72 | Melogliptin | Repaglinide |
| E1.73 | Dutogliptin | selected from the group G3 |
| E1.74 | Dutogliptin | Metformin |
| E1.75 | Dutogliptin | Pioglitazone |
| E1.76 | Dutogliptin | Rosiglitazone |
| E1.77 | Dutogliptin | Glibenclamide |
| E1.78 | Dutogliptin | Glimepiride |
| E1.79 | Dutogliptin | Gliquidone |
| E1.80 | Dutogliptin | Nateglinide |
| E1.81 | Dutogliptin | Repaglinide |

In a second embodiment E2 the pharmaceutical compositions, methods and uses according to this invention preferably relate to combinations wherein the DPPIV inhibitor is linagliptin. According to the second embodiment the SGLT2 inhibitor and the third antidiabetic agent are preferably selected according to the entries in the Table 2.

TABLE 2

| Embodiment | SGLT2 Inhibitor | Third Antidiabetic Agent |
|---|---|---|
| E2.1 | selected from the group G1 | selected from the group G3 |
| E2.2 | selected from the group G1 | Metformin |
| E2.3 | selected from the group G1 | Pioglitazone |
| E2.4 | selected from the group G1 | Rosiglitazone |
| E2.5 | selected from the group G1 | Glibenclamide |
| E2.6 | selected from the group G1 | Glimepiride |
| E2.7 | selected from the group G1 | Gliquidone |
| E2.8 | selected from the group G1 | Nateglinide |
| E2.9 | selected from the group G1 | Repaglinide |
| E2.10 | Compound (I.9) | selected from the group G3 |
| E2.11 | Compound (I.9) | Metformin |
| E2.12 | Compound (I.9) | Pioglitazone |
| E2.13 | Compound (I.9) | Rosiglitazone |
| E2.14 | Compound (I.9) | Glibenclamide |
| E2.15 | Compound (I.9) | Glimepiride |
| E2.16 | Compound (I.9) | Gliquidone |
| E2.17 | Compound (I.9) | Nateglinide |
| E2.18 | Compound (I.9) | Repaglinide |
| E2.19 | Dapagliflozin | selected from the group G3 |
| E2.20 | Dapagliflozin | Metformin |
| E2.21 | Dapagliflozin | Pioglitazone |
| E2.22 | Dapagliflozin | Rosiglitazone |
| E2.23 | Dapagliflozin | Glibenclamide |
| E2.24 | Dapagliflozin | Glimepiride |
| E2.25 | Dapagliflozin | Gliquidone |
| E2.26 | Dapagliflozin | Nateglinide |
| E2.27 | Dapagliflozin | Repaglinide |
| E2.28 | Canagliflozin | selected from the group G3 |
| E2.29 | Canagliflozin | Metformin |
| E2.30 | Canagliflozin | Pioglitazone |
| E2.31 | Canagliflozin | Rosiglitazone |
| E2.32 | Canagliflozin | Glibenclamide |
| E2.33 | Canagliflozin | Glimepiride |
| E2.34 | Canagliflozin | Gliquidone |
| E2.35 | Canagliflozin | Nateglinide |
| E2.36 | Canagliflozin | Repaglinide |
| E2.37 | Atigliflozin | selected from the group G3 |
| E2.38 | Atigliflozin | Metformin |
| E2.39 | Atigliflozin | Pioglitazone |
| E2.40 | Atigliflozin | Rosiglitazone |
| E2.41 | Atigliflozin | Glibenclamide |
| E2.42 | Atigliflozin | Glimepiride |
| E2.43 | Atigliflozin | Gliquidone |
| E2.44 | Atigliflozin | Nateglinide |
| E2.45 | Atigliflozin | Repaglinide |
| E2.46 | Remogliflozin | selected from the group G3 |
| E2.47 | Remogliflozin | Metformin |
| E2.48 | Remogliflozin | Pioglitazone |
| E2.49 | Remogliflozin | Rosiglitazone |
| E2.50 | Remogliflozin | Glibenclamide |
| E2.51 | Remogliflozin | Glimepiride |
| E2.52 | Remogliflozin | Gliquidone |
| E2.53 | Remogliflozin | Nateglinide |
| E2.54 | Remogliflozin | Repaglinide |
| E2.55 | Sergliflozin | selected from the group G3 |
| E2.56 | Sergliflozin | Metformin |
| E2.57 | Sergliflozin | Pioglitazone |
| E2.58 | Sergliflozin | Rosiglitazone |
| E2.59 | Sergliflozin | Glibenclamide |
| E2.60 | Sergliflozin | Glimepiride |
| E2.61 | Sergliflozin | Gliquidone |
| E2.62 | Sergliflozin | Nateglinide |
| E2.63 | Sergliflozin | Repaglinide |

Among the combinations according to the present invention listed in Table 1 and Table 2, the combinations No. E1.1 to E1.18 and E2.1 to E2.18, in particular E1.10 to E1.18 and E2.10 to E2.18, especially E1.11 and E2.11 are even more preferred.

The combination of an SGLT2 inhibitor, a DPPIV inhibitor and a third antidiabetic agent according to this invention significantly improves the glycemic control, in particular in patients as described hereinafter, compared with a monotherapy using either a SGLT2 inhibitor or a DPP IV inhibitor or the third antidiabetic agent alone, for example with a monotherapy of metformin. Furthermore the combination of an SGLT2 inhibitor, a DPPIV inhibitor and a third antidiabetic agent according to this invention improves the glycemic control, in particular in patients as described hereinafter, compared with a combination therapy using an SGLT2 inhibitor and a DPP IV inhibitor or using an SGLT2 inhibitor and the third antidiabetic agent or using a DPPIV inhibitor and the third antidiabetic agent. The improved glycemic control is determined as an increased lowering of blood glucose and an increased reduction of HbA1c. With monotherapy in a patient, in particular in patients as described hereinafter, the glycemic control can usually not be further improved significantly by an administration of the drug above a certain highest dose. In addition, a long term treatment using a highest dose may be unwanted in view of potential side effects. Therefore, a satisfying glycemic control cannot be achieved in all patients via a monotherapy using either the SLGT2 inhibitor or the DPP IV inhibitor or the third antidiabetic agent alone. Even with combination therapy using only two agents selected from the SGLT2 inhibitors, DPPIV inhibitors and third antidiabetic agents may not yield in a full glycemic control in all patients and/or over a long time. In such patients a progression of the diabetes mellitus may continue and complications associated with diabetes mellitus may occur, such as macrovascular complications. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy or a therapy using only two of the combination partners.

In addition, the combination of an SGLT2 inhibitor, a DPP IV inhibitor and the third therapeutic agent according to this invention allows a reduction in the dose of either the SGLT2 inhibitor, the DPP IV inhibitor or the third antidiabetic agent or even of two or three of the active ingredients. A dose reduction is beneficial for patients which otherwise would potentially suffer from side effects in a therapy using a higher dose of one or more of the active ingredients, in particular with regard to side effect caused by the third antidiabetic agent. Therefore, the pharmaceutical composition as well as the methods according to the present invention, show less side effects, thereby making the therapy more tolerable and improving the patients compliance with the treatment.

A monotherapy using a DPP IV inhibitor or a combination therapy using a DPPIV inhibitor and a third antidiabetic agent according to the present invention is not independent from the insulin secretory capacity or the insulin sensitivity of a patient. On the other hand, a treatment with the administration of a SGLT2 inhibitor according the present invention does not depend on the insulin secretory capacity or the insulin sensitivity of the patient. Therefore, any patient independent of the prevailing insulin levels or insulin resistance and/or hyperinsulinemia may benefit from a therapy using a combination of a SGLT2 inhibitor with a DPPIV inhibitor and a third antidiabetic agent according to this invention. Independent of their prevailing insulin levels or their insulin resistance or hyperinsulinemia these patients can still be treated with a combination of the DPP IV inhibitor and the third antidiabetic agent because of the combined or alternate administration of the SGLT2 inhibitor.

A DPP IV inhibitor according to the present invention is able—via the increases in active GLP-1 levels—to reduce the glucagon secretion in a patient. This will therefore limit the hepatic glucose production. Furthermore, the elevated active GLP-1 levels produced by the DPP IV inhibitor will have beneficial effects on beta-cell regeneration and neogenesis. All these features of DPP IV inhibitors render a combination with a SGLT2 inhibitor quite useful and therapeutically relevant.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 10 to 17 years, preferably of age 13 to 17 years. It is assumed that in a adolescent population the administration of the pharmaceutical composition according to the invention a very good HbA1c lowering and a very good lowering of the fasting plasma glucose can be seen. In addition it is assumed that in an adolescent population, in particular in overweight and/or obese patients, a pronounced weight loss can be observed.

As described hereinbefore by the administration of the pharmaceutical composition according to this invention and in particular in view of the high SGLT2 inhibitory activity of the SGLT2 inhibitors therein, excessive blood glucose is excreted through the urine of the patient, so that no gain in weight or even a reduction in body weight may result. Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. Any weight increasing effect in the therapy, for example due to the administration of the third antidiabetic agent, may be attenuated or even avoided thereby.

The pharmaceutical composition according to this invention and in particular the SGLT2 inhibitor therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 1.0%, more preferably equal to or greater than 2.0%, even more preferably equal to or greater than 3.0% can be achieved and the reduction is particularly in the range from 1.0% to 3.0%.

Furthermore, the method and/or use according to this invention is advantageously applicable in those patients who show one, two or more of the following conditions:
(a) a fasting blood glucose or serum glucose concentration greater than 100 mg/dL or 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that an SGLT2 inhibitor, a DPPIV inhibitor and a third antidiabetic agent as defined hereinbefore and hereinafter are administered, for example in combination or alternation, to the patient.

According to another preferred embodiment of the present invention, there is provided a method for improving glycemic control in patients, in particular in adult patients, with type 2 diabetes mellitus as an adjunct to diet and exercise.

It can be found that by using a pharmaceutical composition according to this invention, an improvement of the glycemic control can be achieved even in those patients who have insufficient glycemic control in particular despite treatment with an antidiabetic drug, for example despite maximal recommended or tolerated dose of oral monotherapy with metformin, a SGLT2 inhibitor or a DPPIV inhibitor or a combination of metformin with a SGLT2 inhibitor or a combination of metformin with a DPPIV inhibitor, in particular a SGLT2 inhibitor according to this invention, or a DPP IV inhibitor according to this invention. A maximal recommended or tolerated dose with regard to metformin is for example 2000 mg per day, 1500 mg per day (for example in asian countries) or 850 mg three times a day or any equivalent thereof. A maximal recommended or tolerated dose with regard to a SGLT2 inhibitor according to this invention, in particular with regard to the compound (I.9), is for example 100 mg or 50 mg or even 25 mg or 10 mg once per day or any equivalent thereof. A maximal recommended or tolerated dose with regard to linagliptin is for example 10 mg, preferably 5 mg once daily or any equivalent thereof. A maximal recommended or tolerated dose with regard to sitagliptin is for example 100 mg once daily or any equivalent thereof.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal recommended or tolerated dose of metformin;
(c) insufficient glycemic control despite oral monotherapy with the third antidiabetic agent, in particular despite oral monotherpy at a maximal recommended or tolerated dose of the third antidiabetic agent;
(d) insufficient glycemic control despite oral monotherapy with the SGLT2 inhibitor, in particular despite oral monotherpy at a maximal recommended or tolerated dose of the SGLT2 inhibitor;
(e) insufficient glycemic control despite oral monotherapy with the DPPIV inhibitor, in particular despite oral monotherpy at a maximal recommended or tolerated dose of the DPPIV inhibitor;
(f) insufficient glycemic control despite combination therapy with two agents selected from the group of the SGLT2 inhibitor, the DPPIV inhibitor and the third antidiabetic agent;
(g) insufficient glycemic control despite oral combination therapy with the SGLT2 inhibitor and the third antidiabetic agent (for example metformin), in particular despite oral monotherpy at a maximal recommended or tolerated dose of at least one of the combination partners;
(h) insufficient glycemic control despite oral combination therapy with the DPPIV inhibitor and the third antidiabetic agent (for example metformin), in particular despite oral monotherpy at a maximal recommended or tolerated dose of at least one of the combination partners.

The lowering of the blood glucose level by the administration of an SGLT2 inhibitor according to this invention is insulin-independent. Therefore, a pharmaceutical composition according to this invention is particularly suitable in the treatment of patients who are diagnosed having one or more of the following conditions
insulin resistance,
hyperinsulinemia,
pre-diabetes,
type 2 diabetes mellitus, particular having a late stage type 2 diabetes mellitus,
type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level 150 mg/dL,
(c) HDL-cholesterol blood level <40 mg/dL in female patients and <50 mg/dL in male patients,
(d) a systolic blood pressure 130 mm Hg and a diastolic blood pressure 85 mm Hg,
(e) a fasting blood glucose level 100 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

Furthermore, the pharmaceutical composition and the methods according to this invention are particularly suitable in the treatment of patients after organ transplantation, in particular those patients who are diagnosed having one or more of the following conditions
(a) a higher age, in particular above 50 years,
(b) male gender;
(c) overweight, obesity (including class I, II and/or III obesity), visceral obesity and/or abdominal obesity,
(d) pre-transplant diabetes,
(e) immunosuppression therapy.

Furthermore, the pharmaceutical composition and the methods according to this invention are particularly suitable in the treatment of patients who are diagnosed having one or more of the following conditions:
(a) hyponatremia, in particular chronical hyponatremia;
(b) water intoxication;
(c) water retention;
(d) plasma sodium concentration below 135 mmol/L.

The patient may be a diabetic or non-diabetic mammal, in particular human.

Furthermore, the pharmaceutical composition and the methods according to this invention are particularly suitable in the treatment of patients who are diagnosed having one or more of the following conditions:
(a) high serum uric acid levels, in particular greater than 6.0 mg/dL (357 μmol/L);
(b) a history of gouty arthritis, in particular recurrent gouty arthritis;
(c) kidney stones, in particular recurrent kidney stones;
(d) a high propensity for kidney stone formation.

A pharmaceutical composition according to this invention, in particular due to the SGLT2 inhibitor and the DPPIV inhibitor therein, exhibits a good safety profile. Therefore, a treatment or prophylaxis according to this invention is advantageously possible in those patients for which the mono-therapy with another antidiabetic drug, such as for example metformin, is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

The effects mentioned above are observed both, when the SGLT2 inhibitor, the DPP IV inhibitor and the third antidiabetic agent are administered in combination, for example simultaneously in one single or two or three separate formulations, and when they are administered in alternation, for example successively in two or three separate formulations.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor, the DPP IV inhibitor and the third antidiabetic agent according to this invention are included in the pharmaceutical composition or dosage form in an amount sufficient that by their administration in combination and/or alternation the glycemic control in the patient to be treated is improved.

For the treatment of hyperuricemia or hyperuricemia associated conditions the SGLT2 inhibitor according to this invention is included in the pharmaceutical composition or dosage form in an amount sufficient that is sufficient to treat hyperuricemia without disturbing the patient's plasma glucose homeostasis, in particular without inducing hypoglycemia.

For the treatment or prevention of kidney stones the SGLT2 inhibitor according to this invention is included in the pharmaceutical composition or dosage form in an amount sufficient that is sufficient to treat or prevent kidney stones without disturbing the patient's plasma glucose homeostasis, in particular without inducing hypoglycemia.

For the treatment of hyponatremia and associated conditions the SGLT2 inhibitor according to this invention is included in the pharmaceutical composition or dosage form in an amount sufficient that is sufficient to treat hyponatremia or the associated conditions without disturbing the patient's plasma glucose homeostasis, in particular without inducing hypoglycemia.

In the following preferred ranges of the amount of the SGLT2 inhibitor, the DPP IV inhibitor and the third antidiabetic agent to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. The ranges of the dosage and amounts are calculated for the individual active moiety. Advantageously, the combination therapy according to the present invention utilizes lower dosages of the individual SGLT2 inhibitor, of the individual DPP IV inhibitor and/or of the individual third antidiabetic agent used in monotherapy or used in conventional therapeutics, thus avoiding possible toxicity and adverse side effects incurred when those agents are used as monotherapies.

Within the scope of the present invention, the pharmaceutical composition is preferably administered orally. Other forms of administration are possible and described hereinafter. Preferably the one or more dosage forms comprising the SGLT2 inhibitor, the DPPIV inhibitor and/or the third antidiabetic agent is oral or usually well known.

In general, the amount of the SGLT2 inhibitor in the pharmaceutical composition and methods according to this invention is preferably in the range from 1/5 to 1/1 of the amount usually recommended for a monotherapy using said SGLT2 inhibitor.

The preferred dosage range of the SGLT2 inhibitor is in the range from 0.5 mg to 200 mg, even more preferably from 1 to 100 mg, most preferably from 1 to 50 mg per day. The oral administration is preferred. Therefore, a pharmaceutical composition may comprise the hereinbefore mentioned amounts, in particular from 1 to 50 mg or 1 to 25 mg. Particular dosage strengths (e.g. per tablet or capsule) are for example 1, 2.5, 5, 7.5, 10, 12.5, 15, 20, or 50 mg of the compound of the formula (I), in particular of the compound (I.9), or of dapagliflozin. The application of the active ingredient may occur up to three times a day, preferably one or two times a day.

In general, the amount of the DPP IV inhibitor in the pharmaceutical composition and methods according to this invention is preferably in the range from 1/5 to 1/1 of the amount usually recommended for a monotherapy using said DPP IV inhibitor.

A preferred dosage range of linagliptin when administered orally is 0.5 mg to 10 mg per day, preferably 2.5 mg to 10 mg, most preferably 1 mg to 5 mg per day. The preferred range of amounts in the pharmaceutical composition is 0.5 to 10 mg, in particular 1 to 5 mg. Examples of particular dosage strengths are 1, 2.5, 5 or 10 mg. The application of the active ingredient may occur up to three times a day, preferably one or two times a day. Suitable formulations for linagliptin may be those formulations disclosed in the application WO 2007/128724, the disclosure of which is incorporated herein in its entirety.

A preferred dosage range of sitagliptin when administered orally is from 10 to 200 mg, in particular 25 to 150 mg per day. A recommended dose of sitagliptin is 100 mg calculated for the active moiety (free base anhydrate) once daily or 50 mg twice daily. The preferred range of amounts in the pharmaceutical composition is 10 to 150 mg, in particular 25 to 100 mg. Examples are 25, 50, 75 or 100 mg. The application of the active ingredient may occur up to three times a day, preferably one or two times a day. Equivalent amounts of salts of sitagliptin, in particular of the phosphate monohydrate can be calculated accordingly. Adjusted dosages of sitagliptin, for example 25 and 50 mg, are preferably used for patients with renal failure.

A preferred dosage range of vildagliptin when administered orally is from 10 to 150 mg daily, in particular from 25 to 150 mg, 25 and 100 mg or 25 and 50 mg or 50 and 100 mg daily. For example the daily administration of vildagliptin is 50 or 100 mg. The preferred range of amounts in the pharmaceutical composition is 10 to 150 mg, in particular 25 to 100 mg. Examples are 25, 50, 75 or 100 mg. The application of the active ingredient may occur up to three times a day, preferably one or two times a day.

A preferred dosage range of alogliptin when administered orally is from 5 to 250 mg daily, in particular from 10 to 150 mg daily. The preferred range of amounts in the pharmaceutical composition is 5 to 150 mg, in particular 10 to 100 mg. Examples are 10, 12.5, 20, 25, 50, 75 and 100 mg. The application of the active ingredient may occur up to three times a day, preferably one or two times a day.

A preferred dosage range of saxagliptin when administered orally is from 2.5 to 100 mg daily, in particular from 2.5 to 50 mg daily. The preferred range of amounts in the pharmaceutical composition is from 2.5 to 100 mg, in particular from 2.5 and 50 mg. Examples are 2.5, 5, 10, 15, 20, 30, 40, 50 and 100 mg. The application of the active ingredient may occur up to three times a day, preferably one or two times a day.

A preferred dosage range of dutogliptin when administered orally is from 50 to 400 mg daily, in particular from 100 to 400 mg daily. The preferred range of amounts in the pharmaceutical composition is from 50 to 400 mg. Examples are 50, 100, 200, 300 and 400 mg. The application of the active ingredient may occur up to three times a day, preferably one or two times a day.

In general, the amount of the third antidiabetic agent in the pharmaceutical composition and methods according to this invention is preferably in the range from 1/5 to 1/1 of the amount usually recommended for a monotherapy using said antidiabetic agent. Using lower dosages of the individual third antidiabetic agent compared with monotherapy could avoid or minimize possible toxicity and adverse side effects incurred when those agents are used as monotherapies.

A preferred dosage range of metformin when administered orally is 250 to 3000 mg, in particular 500 to 2000 mg per day. The preferred range of amounts in the pharmaceutical composition is 250 to 1000, in particular 500 to 1000 mg or 250 to 850 mg respectively. Examples are 500, 750, 850 or 1000 mg. Preferably the administration of said amounts is once, twice or three times daily. For example the amounts of 500, 750 and 850 mg preferably require once-daily, twice-daily or three-times daily dosing and the amount of 1000 mg preferably requires once-daily or twice-daily dosing. Certain controlled or sustained release formulations allow a once-daily dosing. Metformin can be administered for example in the form as marketed under the trademarks GLUCOPHAGE™, GLUCOPHAGE-D™ or GLUCOPHAGE-XR™.

A preferred dosage range of pioglitazone when administered orally is 5 to 50 mg per day. The preferred range of amounts in the pharmaceutical composition is 5 to 50 mg, 10 to 45 mg and 15 to 45 mg respectively. Examples are 15, 30 or 45 mg. Preferably the administration of said amounts is once or twice daily, in particular once daily. Pioglitazone can be administered in the form as it is marketed for example under the trademark ACTOS™.

A preferred dosage range of rosiglitazone when administered orally is 1 mg to 10 mg per day. The preferred range of amounts in the pharmaceutical composition is 1 to 10 mg, 2 to 8 mg, 4 to 8 mg and 1 to 4 mg. Examples are 1, 2, 4 or 8 mg. Preferably the administration of said amounts is once or twice daily. Preferably the dose should not exceed 8 mg daily. Rosiglitazone can be administered in the form as it is marketed for example under the trademark AVANDIA™.

A preferred dosage range of a thiazolidindione (other than pioglitazone or rosiglitazone as described above) when administered orally is 2 to 100 mg per day. The preferred range of amounts in the pharmaceutical composition for an administration once, twice or three times daily is 2 to 100, 1 to 50 and 1 to 33 mg respectively.

A preferred dosage range of glibenclamide when administered orally is 0.5 to 15 mg, in particular 1 to 10 mg per day. The preferred range of amounts in the pharmaceutical composition is 0.5 to 5 mg, in particular 1 to 4 mg. Examples are 1.0, 1.75 and 3.5 mg. Preferably the administration of said amounts is once, twice or three-times daily. Glibenclamide can be administered in the form as it is marketed for example under the trademark EUGLUCON™.

A preferred dosage range of glimepiride when administered orally is 0.5 to 10 mg, in particular 1 to 6 mg per day. The preferred range of amounts in the pharmaceutical composition is 0.5 to 10 mg, in particular 1 to 6 mg. Examples are 1, 2, 3, 4, and 6 mg. Preferably the administration of said amounts is once, twice or three-times daily, preferably once daily. Glimepiride can be administered in the form as it is marketed for example under the trademark AMARYL™.

A preferred dosage range of gliquidone when administered orally is 5 to 150 mg, in particular to 120 mg per day. The preferred range of amounts in the pharmaceutical composition is 5 to 120 mg, in particular 5 to 30 mg. Examples are 10, 20, 30 mg. Preferably the administration of said amounts is once, twice, three-times or four-times daily. Gliquidone can be administered in the form as it is marketed for example under the trademark GLURENORM™.

A preferred dosage range of glibornuride when administered orally is 5 to 75 mg per day. The preferred range of amounts in the pharmaceutical composition is 5 to 75 mg, in particular 10 to 50 mg. Preferably the administration of said amounts is once, twice or three-times daily.

A preferred dosage range of gliclazide when administered orally is 20 to 300 mg, in particular 40 to 240 mg per day. The preferred range of amounts in the pharmaceutical composition is 20 to 240 mg, in particular 20 to 80 mg. Examples are 20, 30, 40 and 50 mg. Preferably the administration of said amounts is once, twice or three-times daily.

A preferred dosage range of glisoxepide when administered orally is 1 to 20 mg, in particular 1 to 16 mg per day. The preferred range of amounts in the pharmaceutical composition is 1 to 8 mg, in particular 1 to 4 mg. Preferably the administration of said amounts is once, twice, three-times or four-times daily.

A preferred dosage range of tolbutamide when administered orally is 100 to 3000 mg, preferably 500 to 2000 mg per day. The preferred range of amounts in the pharmaceutical composition is 100 to 1000 mg. Preferably the administration of said amounts is once or twice daily.

A preferred dosage range of glipizide when administered orally is 1 to 50 mg, in particular 2.5 to 40 mg per day. The preferred range of amounts in the pharmaceutical composition for an administration once, twice or three times daily is 1 to 50, 0.5 to 25 and 0.3 to 17 mg respectively.

A preferred dosage range of nateglinide when administered orally is 30 to 500 mg, in particular 60 to 360 mg per day. The preferred range of amounts in the pharmaceutical composition is 30 to 120 mg. Examples are 30, 60 and 120 mg. Preferably the administration of said amounts is once, twice or three-times daily. Nateglinide can be administered in the form as it is marketed for example under the trademark STARLIX™.

A preferred dosage range of repaglinide when administered orally is 0.1 to 16 mg, in particular 0.5 to 6 mg per day. The preferred range of amounts in the pharmaceutical composition is 0.5 to 4 mg. Examples are 0.5, 1, 2 or 4 mg. Preferably the administration of said amounts is once, twice, three-times or four-times daily. Repaglinide can be administered in the form as it is marketed for example under the trademark NOVONORM™.

A preferred dosage range of acarbose when administered orally is 50 to 1000 mg, in particular 50 to 600 mg per day. The preferred range of amounts in the pharmaceutical composition is 50 to 150 mg. Examples are 50 and 100 mg. Preferably the administration of said amounts is once, twice, three-times or four-times daily. Acarbose can be administered in the form as it is marketed for example under the trademark Glucobay™.

A preferred dosage range of voglibose when administered orally is 100 to 1000 mg, in particular 200 to 600 mg per day. The preferred range of amounts in the pharmaceutical composition is 50 to 300 mg. Examples are 50, 100, 150, 200 and 300 mg. Preferably the administration of said amounts is once, twice, three-times or four-times daily. Voglibose can be administered in the form as it is marketed for example under the trademark Basen™ or Voglisan™.

A preferred dosage range of miglitol when administered orally is 25 to 500 mg, in particular 25 to 300 mg per day. The preferred range of amounts in the pharmaceutical composition is 25 to 100 mg. Examples are 25, 50 and 100 mg.

Preferably the administration of said amounts is once, twice, three-times or four-times daily. Miglitol can be administered in the form as it is marketed for example under the trademark Glyset™.

A preferred dosage range of GLP-1 analogues, in particular of exenatide is 5 to 30 μg, in particular 5 to 20 μg per day. The preferred range of amounts in the pharmaceutical composition is 5 to 10 μg. Examples are 5 and 10 μg. Preferably the administration of said amounts is once, twice, three-times or four-times daily by subcutaneous injection. Exenatide can be administered in the form as it is marketed for example under the trademark Byetta™. A long acting formulation, preferably for a once weekly subcutaneous injection, comprises an amount from 0.1 to 3.0 mg, preferably 0.5 to 2.0 mg exenatide. Examples are 0.8 mg and 2.0 mg. An example of a long acting formulation of exenatide is Byetta LAR™.

A preferred dosage range of liraglutide is 0.5 to 3 mg, in particular 0.5 to 2 mg per day. The preferred range of amounts in the pharmaceutical composition is 0.5 to 2 mg. Examples are 0.6, 1.2 and 1.8 mg. Preferably the administration of said amounts is once or twice daily by subcutaneous injection.

The amount of the SGLT2 inhibitor, the DPP IV inhibitor and the third therapeutic agent in the pharmaceutical composition and in the methods and uses according to this invention correspond to the respective dosage ranges as provided hereinbefore. For example, preferred dosage ranges in a pharmaceutical composition and in methods and uses according to this invention are an amount of 1 to 50 mg (in particular 1 to 25 mg) of a SGLT2 inhibitor according to the formula (I), in particular of the compound (I.9), an amount of 0.5 to 10 mg (in particular 1 to 5 mg) of linagliptin and an amount of 250 to 1000 mg (in particular 250 to 850 mg) of metformin. An oral administration once or twice daily is preferred.

Another example of preferred dosage ranges in a pharmaceutical composition or in methods or uses according to this invention are an amount of 1 to 50 mg (in particular 1 to 25 mg) of a SGLT2 inhibitor according to the formula (I), in particular of the compound (I.9), an amount of 0.5 to 10 mg (in particular 1 to 5 mg) of linagliptin and an amount of 5 to 50 mg (in particular 10 to 45 mg) of pioglitazone. An oral administration once daily is preferred.

Another example of preferred dosage ranges in a pharmaceutical composition or in methods or uses according to this invention are an amount of 1 to 50 mg (in particular 1 to 25 mg) of dapagliflozin, an amount of 0.5 to 10 mg (in particular 1 to 5 mg) of linagliptin and an amount of 250 to 1000 mg (in particular 250 to 850 mg) of metformin. An oral administration once or twice daily is preferred.

Another example of preferred dosage ranges in a pharmaceutical composition or in methods or uses according to this invention are an amount of 1 to 50 mg (in particular 1 to 25 mg) of a SGLT2 inhibitor according to the formula (I), in particular of the compound (I.9), an amount of 10 to 150 mg (in particular 25 to 100 mg) of vildagliptin and an amount of 250 to 1000 mg (in particular 250 to 850 mg) of metformin. An oral administration once or twice daily is preferred.

Another example of preferred dosage ranges in a pharmaceutical composition or in methods or uses according to this invention are an amount of 1 to 50 mg (in particular 1 to 25 mg) of a SGLT2 inhibitor according to the formula (I), in particular of the compound (I.9), an amount of 5 to 150 mg (in particular 10 to 100 mg) of alogliptin and an amount of 250 to 1000 mg (in particular 250 to 850 mg) of metformin. An oral administration once or twice daily is preferred.

Another example of preferred dosage ranges in a pharmaceutical composition or in methods or uses according to this invention are an amount of 1 to 50 mg (in particular 1 to 25 mg) of a SGLT2 inhibitor according to the formula (I), in particular of the compound (I.9), an amount of 2.5 to 100 mg (in particular 2.5 to 50 mg) of saxagliptin and an amount of 250 to 1000 mg (in particular 250 to 850 mg) of metformin. An oral administration once or twice daily is preferred.

In the methods and uses according to the present invention the SGLT2 inhibitor and the DPP IV inhibitor and the third therapeutic agent are administered in combination or alternation. The term "administration in combination" means that the active ingredients are administered at the same time, i.e. simultaneously, or essentially at the same time. The term "administration in alternation" means that at first one or two active ingredients are administered and after a period of time the other two or one active ingredients are administered, i.e. at least two of the three active ingredients are administered sequentially. The period of time may be in the range from 30 min to 12 hours. The administration which is in combination or in alternation may be once, twice, three times or four times daily, preferably once or twice daily.

With regard to the administration of the SGLT2 inhibitor and the DPP IV inhibitor and the third antidiabetic agent, all three active ingredients may be present in one single dosage form, for example in one tablet or capsule, or one or two of the active ingredients may be present in a separate dosage form, for example in two different or identical dosage forms.

With regard to their administration in alternation, one or two of the active ingredients are present in a separate dosage form, for example in two different or identical dosage forms.

Therefore, the pharmaceutical composition according to this invention may be present as single dosage forms which comprise the SGLT2 inhibitor, the DPP IV inhibitor and the third antidiabetic agent. Alternatively the pharmaceutical composition according to this invention may be present as two separate dosage forms wherein one dosage form comprises the SGLT2 inhibitor and the other dosage form comprises the DPP IV inhibitor plus the third antidiabetic agent or one dosage form comprises the SGLT2 inhibitor plus the third antidiabetic agent and the other dosage form comprises the DPP IV inhibitor. Alternatively the pharmaceutical composition according to this invention may be present as three separate dosage forms wherein one dosage form comprises the SGLT2 inhibitor and a second dosage form comprises the DPP IV inhibitor and the third dosage form comprises the third antidiabetic agent.

Therefore according to one embodiment the pharmaceutical composition according to the invention is characterized in that the SGLT2 inhibitor and the DPP IV inhibitor are present in a single dosage form and the third antidiabetic agent is present in a separate dosage form.

According to another embodiment the pharmaceutical composition according to the invention is characterized in that the SGLT2 inhibitor and the third antidiabetic agent are present in a single dosage form and the DPPIV inhibitor is present in a separate dosage form.

According to another embodiment the pharmaceutical composition according to the invention is characterized in that the DPPIV inhibitor and the third antidiabetic agent are present in a single dosage form and the SGLT2 inhibitor is present in a separate dosage form.

According to another embodiment the pharmaceutical composition according to the invention is characterized in that the SGLT2 inhibitor, the DPP IV inhibitor and the third antidiabetic agent are present in a single dosage form.

According to another embodiment the pharmaceutical composition according to the invention is characterized in that the SGLT2 inhibitor, the DPP IV inhibitor and the third antidiabetic agent are present each in a separate dosage form.

The case may arise in which one active ingredient has to be administered more often, for example twice per day, than the other active ingredients, which for example needs administration once daily. Therefore the term "administration in combination or alternation" also includes an administration scheme in which first all active ingredients are administered in combination or alternation and after a period of time only one active ingredient is administered again or vice versa.

Therefore, the present invention also includes pharmaceutical compositions which are present in separate dosage forms wherein one dosage form comprises SGLT2 inhibitor, the DPP IV inhibitor and the third therapeutic agent and the other dosage form comprises the third therapeutic agent only.

A pharmaceutical composition which is present as a separate or multiple dosage form, preferably as a kit of parts, is useful in combination therapy to flexibly suit the individual therapeutic needs of the patient.

According to a first embodiment a preferred kit of parts comprises
(a) a first containment containing a dosage form comprising the SGLT2 inhibitor and at least one pharmaceutically acceptable carrier, and
(b) a second containment containing a dosage form comprising the DPP IV inhibitor and at least one pharmaceutically acceptable carrier, and
(b) a second containment containing a dosage form comprising the third antidiabetic agent and at least one pharmaceutically acceptable carrier.

According to a second embodiment a preferred kit of parts comprises
(a) a first containment containing a dosage form comprising the SGLT2 inhibitor and the third antidiabetic agent and at least one pharmaceutically acceptable carrier, and
(b) a second containment containing a dosage form comprising the DPP IV inhibitor and at least one pharmaceutically acceptable carrier.

According to a third embodiment a preferred kit of parts comprises
(a) a first containment containing a dosage form comprising the SGLT2 inhibitor and at least one pharmaceutically acceptable carrier, and
(b) a second containment containing a dosage form comprising the DPP IV inhibitor and the third antidiabetic agent and at least one pharmaceutically acceptable carrier.

According to a fourth embodiment a preferred kit of parts comprises
(a) a first containment containing a dosage form comprising the SGLT2 inhibitor and the DPPIV inhibitor and at least one pharmaceutically acceptable carrier, and
(b) a second containment containing a dosage form comprising the third antidiabetic agent and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

According to a first embodiment a manufacture comprises (a) a pharmaceutical composition comprising a SGLT2 inhibitor according to the present invention and (b) a label or package insert which comprises instructions that the medicament may or is to be administered, for example in combination or alternation, with a medicament comprising a DPP IV inhibitor according to the present invention and with a medicament comprising a third antidiabetic agent according to the present invention or with a medicament comprising both a DPPIV inhibitor and a third antidiabetic agent according to the present invention.

According to a second embodiment a manufacture comprises (a) a pharmaceutical composition comprising a DPP IV inhibitor according to the present invention and (b) a label or package insert which comprises instructions that the medicament may or is to be administered, for example in combination or alternation, with a medicament comprising a SGLT2 inhibitor according to the present invention and a medicament comprising a third antidiabetic agent according to the present invention or with a medicament comprising both a SGLT2 inhibitor and a third antidiabetic agent according to the present invention.

According to a third embodiment a manufacture comprises (a) a pharmaceutical composition comprising a DPP IV inhibitor and a third antidiabetic agent according to the present invention and (b) a label or package insert which comprises instructions that the medicament may or is to be administered, for example in combination or alternation, with a medicament comprising a SGLT2 inhibitor according to the present invention.

According to a fourth embodiment a manufacture comprises (a) a pharmaceutical composition comprising a SGLT2 inhibitor and a third antidiabetic agent according to the present invention and (b) a label or package insert which comprises instructions that the medicament may or is to be administered, for example in combination or alternation, with a medicament comprising a DPPIV inhibitor according to the present invention.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, subcutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers. Preferred carriers must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore compared with pharmaceutical compositions and methods which comprise only one or two of the three active ingredients. Advantageous effects may be seen for example with respect to efficacy, dosage strength, dosage frequency, pharmacodynamic properties, pharmacokinetic properties, fewer adverse effects, convenience, compliance, etc.

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to the preferred compound (I.9) an advantageous crystalline form is described in the international patent application WO 2006/117359 which hereby is incorporated herein in its entirety.

With respect to linagliptin, the methods of synthesis are known to the skilled person and as described in the literature, in particular as described in WO 2002/068420, WO 2004/018468, or WO 2006/048427, the disclosures of which are incorporated herein. Polymorphous crystal modifications and formulations of particular DPP IV inhibitors are disclosed in WO 2007/128721 and WO 2007/128724, respectively, the disclosures of which are incorporated herein in their entireties.

The methods of synthesis for the further DPP IV inhibitors are described in the scientific literature and/or in published patent documents, particularly in those cited hereinbefore.

The active ingredients, in particular the DPP IV inhibitor and/or the third antidiabetic agent, may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

Any of the above mentioned combinations and methods within the scope of the invention may be tested by animal models known in the art. In the following, in vivo experiments are described which are suitable to evaluate pharmacologically relevant properties of pharmaceutical compositions and methods according to this invention:

Pharmaceutical compositions and methods according to this invention can be tested in genetically hyperinsulinemic or diabetic animals like db/db mice, ob/ob mice, Zucker Fatty (fa/fa) rats or Zucker Diabetic Fatty (ZDF) rats. In addition, they can be tested in animals with experimentally induced diabetes like HanWistar or Sprague Dawley rats pretreated with streptozotocin.

The effect on glycemic control of the combinations according to this invention can be tested after single dosing of the SGLT2 inhibitor and the DPP IV inhibitor and the third antidiabetic agent alone and in combination in an oral glucose tolerance test in the animal models described hereinbefore. The time course of blood glucose is followed after an oral glucose challenge in overnight fasted animals. The combinations according to the present invention significantly improve glucose excursion compared to each monotherapy or dual-combination therapy using a combination of only two of the three active ingredients as measured by reduction of peak glucose concentrations or reduction of glucose AUC. In addition, after multiple dosing of the SGLT2 inhibitor and the DPP IV inhibitor and the third therapeutic agent alone and in combination in the animal models described hereinbefore, the effect on glycemic control can be determined by measuring the HbA1c value in blood. The combinations according to this invention significantly reduce HbA1c compared to each monotherapy or compared to a dual-combination therapy, i.e. using a combination of only two of the three active ingredients, for example employing the SGLT2 inhibitor plus the third antidiabetic agent or the DPPIV inhibitor and the third therapeutic agent.

The possible dose reduction of one or more of the SGLT2 inhibitor, the DPPIV inhibitor and the third antidiabetic agent can be tested by the effect on glycemic control of lower doses of the combinations and monotherapies or dual-combination therapies in the animal models described hereinbefore. The combinations according to this invention at the lower doses significantly improve glycemic control compared to placebo treatment whereas the monotherapies or dual-combination therapies at lower doses do not.

The improved independence from insulin of the treatment according to this invention can be shown after single dosing in oral glucose tolerance tests in the animal models described hereinbefore. The time course of plasma insulin is followed after a glucose challenge in overnight fasted animals. The SGLT2 inhibitor in combination with the DPP IV inhibitor and the third antidiabetic agent will exhibit lower insulin peak concentrations or insulin AUC at lower blood glucose excursion than the DPP IV inhibitor alone.

The increase in active GLP-1 levels by treatment according to this invention after single or multiple dosing can be determined by measuring those levels in the plasma of animal models described hereinbefore in either the fasting or postprandial state. Likewise, a reduction in glucagon levels in plasma can be measured under the same conditions. The SGLT2 inhibitor in combination with the DPP IV inhibitor and the third antidiabetic agent will exhibit higher active GLP-1 concentrations and lower glucagon concentrations than the SGLT2 inhibitor alone.

A superior effect of the combination of a SGLT2 inhibitor, a DPP IV inhibitor and a third antidiabetic agent according to the present invention on beta-cell regeneration and neogenesis can be determined after multiple dosing in the animal models described hereinbefore by measuring the increase in pancreatic insulin content, or by measuring increased beta-cell mass by morphometric analysis after immunhistochemical staining of pancreatic sections, or by measuring increased glucose-stimulated insulin secretion in isolated pancreatic islets.

Pharmacological Examples

The following examples show the beneficial effect on glycemic control of the combination according to the present invention.

Example 1

According to a first example an oral glucose tolerance test is performed in overnight fasted male Zucker rats (Crl:ZUC (Orl)Lepr$^{fa}$) or Zucker Diabetic Fatty (ZDF) rats (ZDF/Crl-Lepr$^{fa}$/Crl). A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 0.015% Polysorbat 80) or vehicle containing either the SGLT2 inhibitor or the DPPIV inhibitor or the third antidiabetic agent or the combination of the SGLT2 inhibitor plus the DPP IV inhibitor plus the third antidiabetic agent. Alternatively, the test can also be performed after multiple administrations of the respective drugs to account for anti-diabetic effects that need longer to become evident like in the case of thiazolidindiones. The animals receive an oral glucose load (2 g/kg) 30 min after compound administration. Blood glucose is measured in tail blood 30 min, 60 min, 90 min, and 120 min after the glucose challenge. Glucose excursion is quantified by calculating the glucose AUC. The data are presented as mean±SEM. The two-sided unpaired Student t-test is used for statistical comparison of the control group and the active groups. Statistical comparisons are conducted by Student's t test.

The following specific example shows the superior effect on glycemic control of the combination of the SGLT2 inhibitor (I.9) with the DPPIV inhibitor linagliptin and with metformin as a third antidiabetic agent as compared to the respective monotherapies and double combinations. All experimental protocols concerning the use of laboratory animals were reviewed by a federal Ethics Committee and approved by governmental authorities. An oral glucose tolerance test was performed after single oral dosing in overnight fasted male Zucker rats as described above. Control animals received vehicle only. Compound A is the glucopyranosyl-substituted benzene derivative (I.9) at a dose of 0.5 mg/kg body weight. Compound B is linagliptin at a dose of 0.5 mg/kg body weight. Met is metformin at a dose of 50 mg/kg body weight. In the combinations, the compounds were administered together at the same doses as in the respective monotherapies. The result is shown in FIG. 1.

P values for comparison versus control are indicated by symbols above the bars. P values for comparison of the triple combination of the glucopyranosyl-substituted benzene derivative, linagliptin and metformin with the respective double combinations and monotherapies are indicated below the FIGURE (#, p<0.1; *, p<0.05; , p<0.01; *, p<0.001). A p value below 0.05 is considered as being statistically significant, and a p value between 0.1 and 0.05 is regarded as showing a trend. A complete set of p values for comparison of all groups is given in the following Table 3.

|         | A    | B    | Met  | A + Met | B + Met | A + B | A + B + Met |
|---------|------|------|------|---------|---------|-------|-------------|
| Control | n.s. | n.s. | n.s. | #       | *       | *     | **          |
| A       |      | n.s. | n.s. | *       | *       | **    | ***         |
| B       |      |      | n.s. | #       | #       | #     | *           |
| Met     |      |      |      | #       | #       | *     | **          |
| A + Met |      |      |      |         | n.s.    | n.s.  | *           |
| B + Met |      |      |      |         |         | n.s.  | *           |
| A + B   |      |      |      |         |         |       | *           |

None of the compounds used here as monotherapy at a low dose had an effect on glucose tolerance. Surprisingly, it was found that the triple combination of the glucopyranosyl-substituted benzene derivative plus linagliptin plus metformin reduced glucose excursion significantly by 16% versus control, and this reduction in total glucose AUC was also statistically significant not only when compared to each of the monotherapies, but also when compared to each of the double combinations.

Example 2

According to a second example an oral glucose tolerance test is performed in overnight fasted male Sprague Dawley rats (Crl:CD(SD)) with a body weight of about 200 g. A pre-dose blood sample is obtained by tail bleed. Blood glucose is measured with a glucometer, and the animals are randomized for blood glucose (n=5/group). Subsequently, the groups receive a single oral administration of either vehicle alone (0.5% aqueous hydroxyethylcellulose containing 0.015% Polysorbat 80) or vehicle containing either the SGLT2 inhibitor or the DPPIV inhibitor or the third antidiabetic agent or the combination of the SGLT2 inhibitor plus the DPP IV inhibitor plus the third antidiabetic agent. Alternatively the groups receive a single oral administration of either vehicle alone or vehicle containing either the SGLT2 inhibitor or the DPPIV inhibitor plus the third antidiabetic agent or the third antidiabetic agent or the combination of the SGLT2 inhibitor plus the DPP IV inhibitor plus the third antidiabetic agent. Alternatively, the test can also be performed after multiple administrations of the respective drugs to account for anti-diabetic effects that need longer to become evident like in the case of thiazolidindiones. The animals receive an oral glucose load (2 g/kg) 30 min after compound administration. Blood glucose is measured in tail blood 30 min, 60 min, 90 min, and 120 min after the glucose challenge. Glucose excursion is quantified by calculating the glucose AUC. The data are presented as mean±S.E.M. Statistical comparisons are conducted by Student's t test.

Example 3: Treatment of Pre-Diabetes

The efficacy of a pharmaceutical composition according to the invention in the treatment of pre-diabetes characterised by pathological fasting glucose and/or impaired glucose tolerance can be tested using clinical studies. In studies over a shorter period (e.g. 2-4 weeks) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose levels demonstrates the efficacy of the treatment. In studies over a longer period (12 weeks or more) the success of the treatment is tested by determining the HbA1c value, by comparison with the initial value and/or with the value of the placebo group. A significant change in the HbA1c value compared with the initial value and/or the placebo value demonstrates the efficacy of the combination according to the invention for treating pre-diabetes.

Example 4: Preventing Manifest Type 2 Diabetes

Treating patients with pathological fasting glucose and/or impaired glucose tolerance (pre-diabetes) is also in pursuit of the goal of preventing the transition to manifest type 2 diabetes. The efficacy of a treatment can be investigated in a comparative clinical study in which pre-diabetes patients are treated over a lengthy period (e.g. 1-5 years) with either a pharmaceutical composition according to this invention or with placebo or with a non-drug therapy or other medicaments. During and at the end of the therapy, by determining the fasting glucose and/or a loading test (e.g. oGTT), a check is made to determine how many patients exhibit manifest type 2 diabetes, i.e. a fasting glucose level of >125 mg/dl and/or a 2 h value according to oGTT of >199 mg/dl. A significant reduction in the number of patients who exhibit manifest type 2 diabetes when treated with a combination according to this invention as compared to one of the other forms of treatment, demonstrates the efficacy in preventing a transition from pre-diabetes to manifest diabetes.

Example 5: Treatment of Type 2 Diabetes

Treating patients with type 2 diabetes with the pharmaceutical composition according to the invention, in addition to producing an acute improvement in the glucose metabolic situation, prevents a deterioration in the metabolic situation in the long term. This can be observed is patients are treated for a longer period, e.g. 3 months to 1 year or even 1 to 6 years, with the pharmaceutical composition according to the invention and are compared with patients who have been treated with other antidiabetic medicaments. There is evidence of therapeutic success compared with patients treated with other antidiabetic medicaments if no or only a slight increase in the fasting glucose and/or HbA1c value is observed. Further evidence of therapeutic success is obtained if a significantly smaller percentage of the patients treated with a pharmaceutical composition according to the invention, compared with patients who have been treated with other medicaments, undergo a deterioration in the glucose metabolic position (e.g. an increase in the HbA1c value to >6.5% or >7%) to the point where treatment with an additional oral antidiabetic medicament or with insulin or with an insulin analogue is indicated.

Example 6: Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a pharmaceutical composition according to the invention in the treatment of insulin resistance.

Example 7: Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a pharmaceutical composition according to the invention in the treatment of hyperglycaemia.

Example 8: Prevention of Micro- or Macrovascular Complications

The treatment of type 2 diabetes or pre-diabetes patients with a pharmaceutical composition according to the invention prevents or reduces or reduces the risk of developing microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with a pharmaceutical composition according to the invention or a combination of active ingredients according to the invention and compared with patients who have been treated with other antidiabetic medicaments or with placebo. Evidence of the therapeutic success compared with patients who have been treated with other antidiabetic medicaments or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinine clearance, serum creatinin values, time taken for the serum creatinine values to double, time taken until dialysis becomes necessary.

Example 9: Treatment of Metabolic Syndrome

The efficacy of a pharmaceutical composition according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active ingredient or combination of active ingredients in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Example 10a: Prevention of NODAT and/or PTMS, and NODAT/PTMS Associated Complications Treatment of patients after organ transplantation with the pharmaceutical composition according to the invention prevents the development of NODAT and/or PTMS, and associated complications. The efficacy of the treatment can be investigated in a comparative clinical study in which patients before or immediately after transplantation are treated over a lengthy period (e.g. 1-5 years) with either a pharmaceutical composition according to this intervention or with a placebo or with a non-drug therapy or other medicaments. During and at the end of the therapy, the incidence of NODAT, PTMS, micro- and macrovascular complications, graft rejection, infection and death will be assessed. A significant reduction in the number of patients experiencing these complications demonstrates the efficacy in preventing development of NODAT, PTMS, and associated complications.

Example 10b: Treatment of NODAT and/or PTMS with Prevention, Delay or Reduction of Associated Complications Treatment of patients with NODAT and/or PTMS with the pharmaceutical composition according to the invention prevents, delays or reduces the development of NODAT/PTMS associated complications. The efficacy of the treatment can be investigated in a comparative clinical study in which patients with NODAT and/or PTMS are treated over a lengthy period (e.g. 1-5 years) with either a pharmaceutical composition according to this intervention or with a placebo or with a non-drug therapy or other medicaments. During and at the end of the therapy, the incidence of micro- and macrovascular complications, graft rejection, infection and death will be assessed. A significant reduction in the number of patients experiencing these complications demonstrates the efficacy in preventing, delaying or reducing the development of NODAT and/or PTMS associated complications.

Example 11a: Treatment of Gestational Diabetes

In clinical studies running for a shorter period (e.g. 2-4 weeks) the success of the treatment is checked by determining the fasting glucose values and/or the glucose values after a meal or after a loading test (oral glucose tolerance test or food tolerance test after a defined meal) at the end of the therapeutic period of the study and comparing them with the values before the start of the study and/or with those of a placebo group. In addition, the fructosamine value can be determined before and after treatment and compared with the initial value and/or a placebo value. A significant fall in the fasting or non-fasting glucose levels demonstrates the pharmaceutical composition according to the invention.

In longer-running studies (12 weeks or more) the success of the treatment is checked by determining the HbA1c value (compared with initial value and placebo group). A significant change in the HbA1c value compared with the starting value and/or placebo value demonstrates the efficacy of the pharmaceutical composition according to the invention in the treatment of gestational diabetes.

Example 11 b: Treatment of Women Who have had Gestational Diabetes

Patients with gestational diabetes have a significantly increased risk of contracting manifest type 2 diabetes after the pregnancy. Therapy may be provided with the objective of preventing the transition to manifest type 2. For this purpose, women with a history of gestational diabetes are treated either with a pharmaceutical composition according to the invention or with placebo or with a non-drug therapy or with other medicaments, over a lengthy period (e.g. 1-4 years). During and at the end of the treatment a check is carried out by determining the fasting glucose and/or by a loading test (e.g. oGTT) to see how many patients have developed manifest type 2 diabetes (fasting glucose level >125 mg/dl and/or 2 h value after oGTT >199 mg/dl). A significant reduction in the number of patients who develop manifest type 2 diabetes when treated with a pharmaceutical composition according to the invention compared with a different type of therapy, is proof of the efficacy of a pharmaceutical composition in preventing manifest diabetes in women with a history of gestational diabetes.

Example 12: Treatment of Hyperuricemia

Patients with elevated levels of uric acid above the normal range (above 8.3 mg/dL or 494 μmol/L) or patients with a history of gout or gouty arthritis with a uric acid level greater than 6.0 mg/dL or 357 μmol/L have a significant risk of future episodes of gout or gouty arthritis as well as having an increased risk of cardiovascular disease. Therapy may be provided with the objective of lowering serum levels of uric acid as a means of preventing future episodes or flare-ups of gout or gouty arthritis. Additionally, lowering serum uric acid levels may reduce the risk of cardiovascular disease. For this purpose patients with an elevated uric acid level or a history of gout or gouty arthritis are treated either with a pharmaceutical composition according to the invention or with placebo or with a non-drug therapy or with other medicaments, over a lengthy period (e.g. 6 months to 4 years). During and at the end of the treatment a check is carried out by determining the serum uric acid level and the number of episodes of gout or gouty arthritis occurrences. A reduction in uric acid below 6.0 mg/dL and/or fewer episodes of gout or gouty arthritis occurrence when treated with a pharmaceutical composition according to the invention compared with a different type of therapy, is proof of the efficacy of a pharmaceutical composition in preventing episodic gout or gouty arthritis or treating hyperuricemia.

Example 13: Treatment of Hyponatremia

Patients with hyponatremia and water intoxication whether due to an increase in water resorption or an increase in water intake, are at risk of central nervous system abnormalities and possibly death. Therapy may be provided with the objective of increasing the amount of free water to be excreted in the renal filtrate without disturbing sodium balance with the objective of increasing the overall sodium concentration of the interstitial fluids. For this purpose, patients with a history of hyponatremia are treated either with a pharmaceutical composition according to the invention or with placebo or with a non-drug therapy or with other medicaments, over a short period (e.g. 3 to 6 months), with periodic assessment of serum sodium levels. An increase in sodium levels into the normal range reported during this time period when treated with a pharmaceutical composition according to the invention compared with a different type of therapy, is proof of the efficacy of a pharmaceutical composition in treating hyponatremia.

Example 14: Treatment/Prevention of Kidney Stones

Patients with a history of kidney stones, particularly calcium, mixed calcium, and uric acid stones frequently have a history of hyperuricemia. These renal stones may relate to small urate crystals forming a nidus in the renal filtrate upon which further crystallization of urate or other crystalizing substances in the solute can induce renal stone formation. These stones are not related to renal stones caused by certain kidney infections (such as staghorn—type stones). Therapy may be provided with the objective of increasing the neutral solutes (for example glucose) and free water content of the renal filtrate, making it difficult for a urate nidus to form, despite a possible increase in the absolute amounts of urate in the renal filtrate. These neutral solutes and free water will also reduce the formation of stones other than uric acid stones. For this purpose patients with a history of kidney stones particularly calcium, mixed calcium, and uric acid stones are treated either with a pharmaceutical composition according to the invention or with placebo or with a non-drug therapy or with other medicaments, over a lengthy period (e.g. 6 months to 4 years). A reduction in the number of kidney stones stones particularly calcium, mixed calcium, and uric acid stones reported during this time period when treated with a pharmaceutical composition according to the invention compared with a different type of therapy, is proof of the efficacy of a pharmaceutical composition in preventing kidney stones particularly calcium, mixed calcium, and uric acid stones.

Examples of Formulations

The following examples of formulations, which may be obtained analogously to methods known in the art, serve to illustrate the present invention more fully without restricting it to the contents of these examples. The term "active ingredient" denotes one or more compounds according to the invention, i.e. denotes an SGLT2 inhibitor, DPP IV inhibitor or a third antidiabetic compound according to this invention or a combination of two or three of said active ingredients, for example selected from the combinations as listed in the Table 1 or 2. Additional suitable formulations for the DPP IV inhibitor linagliptin may be those formulations disclosed in the application WO 2007/128724, the disclosure of which is incorporated herein in its entirety. Additional suitable formulations for the other DPP IV inhibitors may be those formulations which are available on the market, or formulations described in the patent applications cited above in paragraph "background of the invention", or those described in the literature, for example as disclosed in current issues of "Rote Liste" (Germany) or of "Physician's Desk Reference".

Example 1: Dry Ampoule Containing 75 mg of Active Ingredient Per 10 ml

Composition

| | |
|---|---|
| Active ingredient | 75.0 mg |
| Mannitol | 50.0 mg |
| water for injections | ad 10.0 ml |

Preparation

Active ingredient and mannitol are dissolved in water. After packaging the solution is freeze-dried. To produce the solution ready for use, the product is dissolved in water for injections.

Example 2: Dry Ampoule Containing 35 mg of Active Ingredient Per 2 ml

Composition

| | |
|---|---|
| Active ingredient | 35.0 mg |
| Mannitol | 100.0 mg |
| water for injections | ad 2.0 ml |

Preparation

Active ingredient and mannitol are dissolved in water. After packaging, the solution is freeze-dried. To produce the solution ready for use, the product is dissolved in water for injections.

Example 3: Tablet Containing 50 mg of Active Ingredient

Composition

| | | |
|---|---|---|
| (1) | Active ingredient | 50.0 mg |
| (2) | Mannitol | 98.0 mg |
| (3) | Maize starch | 50.0 mg |
| (4) | Polyvinylpyrrolidone | 15.0 mg |
| (5) | Magnesium stearate | 2.0 mg |
| | | 215.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example 4: Tablet Containing 350 mg of Active Ingredient

Preparation

| | | |
|---|---|---|
| (1) | Active ingredient | 350.0 mg |
| (2) | Mannitol | 136.0 mg |
| (3) | Maize starch | 80.0 mg |
| (4) | Polyvinylpyrrolidone | 30.0 mg |
| (5) | Magnesium stearate | 4.0 mg |
| | | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example 5: Tablet Containing 850 mg of Active Ingredient

Preparation

| | | |
|---|---|---|
| (1) | Active ingredient | 850.0 mg |
| (2) | Mannitol | 300.0 mg |
| (3) | Maize starch | 200.0 mg |
| (4) | Polyvinylpyrrolidone | 70.0 mg |
| (5) | Magnesium stearate | 10.0 mg |
| | | 1430.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example 6: Capsules Containing 50 mg of Active Ingredient

Composition

| | | |
|---|---|---|
| (1) | Active ingredient | 50.0 mg |
| (2) | Dried maize starch | 58.0 mg |
| (3) | Mannitol | 50.0 mg |
| (4) | Magnesium stearate | 2.0 mg |
| | | 160.0 mg |

Preparation (1) is triturated with (3). This trituration is added to the mixture of (2) and (4) with vigorous mixing. This powder mixture is packed into size 3 hard gelatin capsules in a capsule filling machine.

Example 7: Capsules Containing 350 mg of Active Ingredient

Composition

| | | |
|---|---|---|
| (1) | Active ingredient | 350.0 mg |
| (2) | Dried maize starch | 46.0 mg |
| (3) | Mannitol | 30.0 mg |
| (4) | Magnesium stearate | 4.0 mg |
| | | 430.0 mg |

Preparation (1) is triturated with (3). This trituration is added to the mixture of (2) and (4) with vigorous mixing. This powder mixture is packed into size 0 hard gelatin capsules in a capsule filling machine.

What is claimed is:

1. A method for slowing the progression of, delaying or treating a metabolic disorder selected from the group consisting of type 2 diabetes mellitus, impaired glucose tolerance, impaired fasting blood glucose, hyperglycemia, postprandial hyperglycemia, overweight, obesity, metabolic syndrome, gestational diabetes, new onset diabetes after transplantation (NODAT) and complications associated therewith, and post-transplant metabolic syndrome (PTMS) and complications associated therewith in a patient in need thereof, the method comprising administering to the patient an SGLT2 inhibitor, a DPP IV inhibitor and a third antidiabetic agent in combination or alternation to the patient,
   wherein
   the SGLT2 inhibitor is 1-chloro-4-(β-D-glucopyranos-1-yl)-2-[4-((S)-tetrahydrofuran-3-yloxy)-benzyl]-benzene,
   the DPPIV inhibitor is linagliptin or a pharmaceutically acceptable salt thereof, and
   the third antidiabetic agent is metformin or a pharmaceutically acceptable salt thereof,
   wherein
   the SGLT2 inhibitor is administered to the patient in a dosage of 1 mg to 50 mg per day, the DPPIV inhibitor is administered to the patient in a dosage of 1 mg to 5 mg per day, and the third antidiabetic agent administered to the patient in a dosage of 500 mg to 2000 mg per day.

2. The method according to claim 1, wherein the SGLT2 inhibitor and the DPP IV inhibitor are present in a single dosage form and the third antidiabetic agent is present in a separate dosage form.

3. The method according to claim 1, wherein the SGLT2 inhibitor and the third antidiabetic agent are present in a single dosage form and the DPPIV inhibitor is present in a separate dosage form.

4. The method according to claim 1, wherein the DPPIV inhibitor and the third antidiabetic agent are present in a single dosage form and the SGLT2 inhibitor is present in a separate dosage form.

5. The method according to claim 1, wherein the SGLT2 inhibitor, the DPP IV inhibitor and the third antidiabetic agent are present each in a separate dosage form.

6. The method according to claim 1, wherein the dosage of the SGLT2 inhibitor is 10 mg or 25 mg per day.

7. The method according to claim 1, wherein the dosage of the DPPIV inhibitor is 5 mg per day.

8. The method according to claim 1, wherein the dosage of the third antidiabetic agent is 500 mg, 750 mg, 850 mg or 1000 mg per day.

9. The method according to claim 1, wherein the SGLT2 inhibitor is administered to the patient once daily.

10. The method according to claim 1, wherein the DPP IV inhibitor is administered to the patient once daily.

11. The method according to claim 1, wherein the third antidiabetic agent is administered to the patient once or twice daily.

12. The method according to claim 1, wherein the method is for treating type 2 diabetes mellitus.

13. A method for improving glycemic control and/or for reducing of fasting plasma glucose, of postprandial plasma glucose and/or of glycosylated hemoglobin HbA1c in a patient in need thereof, the method comprising administering to the patient an SGLT2 inhibitor, a DPP IV inhibitor and a third antidiabetic agent in combination or alternation to the patient, wherein the SGLT2 inhibitor is 1-chloro-4-(β-D-glucopyranos-1-yl)-2-[4-((S)-tetrahydrofuran-3-yloxy)-benzyl]-benzene, the DPPIV inhibitor is linagliptin or a pharmaceutically acceptable salt thereof, and the third antidiabetic agent is metformin or a pharmaceutically acceptable salt thereof, wherein the SGLT2 inhibitor is administered to the patient in a dosage of 1 mg to 50 mg per day the DPPIV inhibitor is administered to the patient in a dosage of 1 mg to 5 mg per day, and the third antidiabetic agent administered to the patient in a dosage of 500 mg to 2000 mg per day.

14. The method according to claim 13, wherein the SGLT2 inhibitor and the DPP IV inhibitor are present in a single dosage form and the third antidiabetic agent is present in a separate dosage form.

15. The method according to claim 13, wherein the SGLT2 inhibitor and the third antidiabetic agent are present in a single dosage form and the DPPIV inhibitor is present in a separate dosage form.

16. The method according to claim 13, wherein the DPPIV inhibitor and the third antidiabetic agent are present in a single dosage form and the SGLT2 inhibitor is present in a separate dosage form.

17. The method according to claim 13, wherein the SGLT2 inhibitor, the DPP IV inhibitor and the third antidiabetic agent are present each in a separate dosage form.

18. The method according to claim 13, wherein the dosage of the SGLT2 inhibitor is 10 mg or 25 mg per day.

19. The method according to claim 13, wherein the dosage of the DPPIV inhibitor is 5 mg per day.

20. The method according to claim 13, wherein the dosage of the third antidiabetic agent is 500 mg, 750 mg, 850 mg or 1000 mg per day.

21. The method according to claim 13, wherein the SGLT2 inhibitor is administered to the patient once daily.

22. The method according to claim 13, wherein the DPP IV inhibitor is administered to the patient once daily.

23. The method according to claim 13, wherein the third antidiabetic agent is administered to the patient once or twice daily.

24. The method according to claim 13, wherein the method is for improving glycemic control in a patient with type 2 diabetes mellitus.

* * * * *